(12) United States Patent
Fichtinger et al.

(10) Patent No.: US 8,948,471 B2
(45) Date of Patent: Feb. 3, 2015

(54) IMAGE REGISTRATION OF MULTIPLE MEDICAL IMAGING MODALITIES USING A MULTIPLE DEGREE-OF-FREEDOM-ENCODED FIDUCIAL DEVICE

(75) Inventors: Gabor Fichtinger, Kingston (CA); Ameet Jain, Briarcliff Manor, NY (US); Tabish Mustufa, Budd Lake, NJ (US); Keenan Wyrobek, Walnut Creek, CA (US); Greg Chirikjian, Towson, MD (US); Yu Zhou, Hicksville, NY (US); Everette C. Burdette, Champaign, IL (US)

(73) Assignees: The John Hopkins University, Baltimore, MD (US); Acoustic MedSystems, Inc., Savoy, IL (US)

( * ) Notice: Subject to any disclaimer, the term of this patent is extended or adjusted under 35 U.S.C. 154(b) by 1935 days.

(21) Appl. No.: 11/998,452

(22) Filed: Nov. 30, 2007

(65) Prior Publication Data

US 2008/0262345 A1  Oct. 23, 2008

Related U.S. Application Data

(63) Continuation of application No. 10/895,398, filed on Jul. 21, 2004, now abandoned.

(60) Provisional application No. 60/488,965, filed on Jul. 21, 2003.

(51) Int. Cl.
*A61B 5/00* (2006.01)
*A61B 6/00* (2006.01)
*A61B 8/12* (2006.01)

(52) U.S. Cl.
CPC . *A61B 6/504* (2013.01); *A61B 8/12* (2013.01); *A61B 6/4417* (2013.01); *A61B 6/5247* (2013.01)
USPC ........... 382/128; 382/131; 382/132; 600/407; 600/424; 600/426; 600/427

(58) Field of Classification Search
CPC .... A61B 6/4417; A61B 6/504; A61B 6/5247; A61B 8/12
USPC .......... 600/407, 424, 426, 427; 382/128, 130, 382/131
See application file for complete search history.

(56) References Cited

U.S. PATENT DOCUMENTS

| | | | |
|---|---|---|---|
| 6,273,858 B1 | 8/2001 | Fox et al. | |
| 6,314,465 B1 * | 11/2001 | Paul et al. | 709/226 |
| 6,468,265 B1 | 10/2002 | Evans et al. | |
| 6,560,354 B1 * | 5/2003 | Maurer et al. | 382/131 |
| 6,711,429 B1 | 3/2004 | Gilboa et al. | |
| 6,775,399 B1 | 8/2004 | Jiang | |
| 7,065,393 B2 | 6/2006 | Sati et al. | |
| 7,221,733 B1 | 5/2007 | Takai et al. | |
| 7,505,809 B2 * | 3/2009 | Strommer et al. | 600/424 |

(Continued)

*Primary Examiner* — Baisakhi Roy
(74) *Attorney, Agent, or Firm* — Venable LLP; Henry J. Daley; George L. Howarah

(57) ABSTRACT

Disclosed is a system and method for registering images from two medical imaging modalities in a six-degree-of-freedom coordinate space, for the purpose of providing real time registered imagery for optimization of medical procedures. The system and method uses fiducial that is visible to the first imager and in a fixed position and orientation relative to the second imager. The first imager may be an X-ray device such as a C-arm fluoroscope, and the second imager may be a Transrectal Ultrasound (TRUS) device.

15 Claims, 20 Drawing Sheets

(56) References Cited

U.S. PATENT DOCUMENTS

| | | |
|---|---|---|
| 7,689,014 B2 * | 3/2010 | Abovitz et al. ............... 382/128 |
| 7,695,683 B2 * | 4/2010 | Quan et al. .................... 422/504 |
| 7,792,345 B2 * | 9/2010 | Taylor et al. .................. 382/128 |
| 7,804,991 B2 * | 9/2010 | Abovitz et al. ............... 382/128 |
| 7,881,767 B2 * | 2/2011 | Strommer et al. ............ 600/407 |
| 2001/0004395 A1 * | 6/2001 | McCrory et al. .............. 378/162 |
| 2002/0049378 A1 * | 4/2002 | Grzeszczuk et al. .......... 600/427 |
| 2002/0143317 A1 * | 10/2002 | Glossop ........................ 604/529 |
| 2004/0049109 A1 | 3/2004 | Thorton |
| 2004/0092786 A1 | 5/2004 | Zaider et al. |
| 2006/0241368 A1 | 10/2006 | Fichtinger et al. |

* cited by examiner

IMAGE REGISTRATION OF MULTIPLE MEDICAL IMAGING MODALITIES USING A MULTIPLE DEGREE-OF-FREEDOM-ENCODED FIDUCIAL DEVICE

This application claims the benefit of U.S. Provisional Patent Application No. 60/488,965, filed on Jul. 21, 2003, and U.S. Non-provisional application Ser. No. 10/895,398, filed on Jul. 21, 2004, both of which are hereby incorporated by reference for all purposes as if fully set forth herein.

Research and development efforts associated with the subject matter of this patent application was supported by the National Science Foundation under Grant No. ERC 9731478, and by the National Institutes of Health under Grant No. 1R43CA099374-01.

BACKGROUND OF THE INVENTION

1. Field of the Invention

The present invention relates to the registration of multiple medical imaging modalities in support of real time optimization of medical procedures. In particular, the invention relates to the registration of ultrasound and C-arm fluoroscopy imagery for these purposes.

Adenocarcinoma of the prostate is the most commonly diagnosed cancer in the U.S. male population. During the last half decade, there have been approximately 200,000 new cases of prostate cancer diagnosed each year, which is comparable to breast cancer diagnosis, and there is no evidence that this number would significantly decrease in the foreseeable future. For several decades, the definitive treatment of low-risk prostate cancer was radical prostatectomy or external beam radiation therapy (EBRT). During the 90's the technique of transrectal ultrasound (TRUS) guided transperineal low dose-rate brachytherapy became a well-proven treatment alternative, comparable to surgery and EBRT, has demonstrated excellent local control rates, and most recent data reports excellent long-term (10-12 year) disease-free survival rates equivalent to radical prostatectomy and external beam radiotherapy. Moreover, studies indicate that there are no unexpected urethral or rectal complications or side effects with low dose-rate brachytherapy.

However, the rate of rectal and urethral complications associated with low dose-rate brachytherapy is still high. The underlying reason for this has predominantly been the lack of adequate visualization and control of the implant process, which leads to improper placement of the implanted radiation source and inaccurate delivery of the sources of radiation dosage. As one skilled in the art will readily appreciate, radioisotopes are used for non-invasive visualization and control processes such as low dose-rate brachytherapy. There have been advances in the ability to use different isotopes to achieve better dose distributions. However, even the best isotope is useless without adequate visualization, localization, and subsequent control of the implanted radiation source. The ability to intraoperatively localize implanted radiation sources (hereinafter "seeds") relative to the prostate is key to enabling dynamic dose calculation during the procedure. The solution of this visualization and control problem would reduce the probability of inaccurately placed implants, thus presenting an opportunity for improved outcomes.

TRUS imaging generally provides satisfactory differentiation of relevant soft issue, but implanted brachytherapy seeds cannot be clearly identified in the TRUS images. Advancements in ultrasound equipment technology are expected to facilitate identification and localization of the seeds in the future, but such equipment will not be available for practitioners in the foreseeable future. On the other hand, currently sixty percent or more of the practitioners use intra-operative C-arm fluoroscopy for purposes of visualization, localization, and control. Although C-arm fluoroscopy, which employs transluminal X-Ray imagery, can accurately localize seeds, it does not differentiate soft tissue. Hence, there is a strong demand for using C-arm fluoroscopy together with a TRUS-guided delivery system.

2. Discussion of the Related Art

Problems and limitations inherent in the related art may be properly illustrated by discussing a particular combination of imaging modalities using C-arm X-ray fluoroscopy and transrectal ultrasound (TRUS). C-arm X-ray fluoroscopy may be the most widely used intra-operative imaging modality in general surgery, and approximately 60+% of the prostate brachytherapy practitioners use it for qualitative implant analysis in the operating room in non-computational qualitative manner. While C-arm fluoroscopy has been used intra-operatively, it has not been utilized in quantitative intra-operative analysis. C-arm has been used as a solo guidance modality. However, since TRUS emerged as a primary image guidance modality, C-arm fluoroscopic x-ray imaging has become a secondary tool for gross visual observation. Very few attempts have been made to relate fluoroscopic images to soft tissue anatomy, and with little success. These attempts have generally used thin metal wire inside a Foley catheter to visualize the prostatic urethra fluoroscopically in anterior-posterior and lateral projections. In other approaches, gold marker seeds have been implanted into the prostate, and the relative positions of the needles and marker seeds have been observed in fluoroscopy.

X-ray radiography has been used extensively for post-implant brachytherapy evaluation using multi-view X-ray to recover seed locations post implant and determine gross dosimetry. Here the fundamental problem is matching a large number of seeds with their projections in multiple X-ray images when some seeds obscure each other and solid objects also can get in the way. Automated methods have been explored, but they also assume conditions that most likely cannot be met with a C-arm fluoroscope, particularly in a realistic intra-operative scenario. Such assumptions include no extrinsic object in the field, optimal beam energy, arbitrary number and orientation of X-ray shots, or unlimited processing time and computational resources—none of which is realistic in real-time image-guided surgery. In conclusion, "off-the-shelf" post-implant seed matching and reconstruction techniques of the related art cannot be expected to work in the operating room. Many approaches have met with great difficulty due to the inability to accurately determine the imaging angles relative to the prostate for reconstruction of the multiple projection images. This not only reduces accuracy, but makes the process too lengthy to be used intraoperatively.

The use of implanted needles as fiducial markers for registration of biplane TRUS data has been explored, but several key problems have been left unsolved. First, the use of implanted needles as fiducials may not be practical, because most practitioners implant only one needle at a time and they do not use stabilizing needles. Second nearly parallel transperineal needles, when used as fiducials, encode weakly in the apex-base direction, with little spatial resolution. Third, because X-ray and TRUS imaging are not simultaneous, it is imperative that the fiducials do not move relative to the prostate until both imaging sessions are complete. For example, during TRUS scanning, the prostate deforms, dislocates, and the needles dislocate relative to the prostate. Fourth, previous attempts at using implanted needles as fiducial markers did not account for the need to pre-operatively calibrate the C-arm fluoroscope, including removing image distortion and some form of intra-operative tracking to know where the multiple X-ray shots are coming with respect to one another.

Accordingly, TRUS guided transperineal low dose-rate brachytherapy has emerged as one of the preferred treatments for low-risk prostate cancer. While ultrasound is generally an excellent tool for guiding the implant needles with respect to prostate anatomy, it cannot reliably show the location of radioactive seeds after they are released in the prostate. Intra-operative C-arm fluoroscopy does adequately show the location of implanted seeds, but it cannot differentiate soft tissue; thus, it cannot be used for visualizing prostate anatomy.

Accordingly, what is needed is intra-operative fusion of these two complementary modalities, which offers significant clinical benefit by allowing for real-time optimization of the brachytherapy implant as the procedure progresses in the operating room.

The problems discussed are not limited to TRUS guided transperineal low dose-rate brachytherapy discussed above, but apply to procedures requiring accurate placement of objects such as surgical tools or implants within a patient. The problems and limitations apply to any procedure in which two imaging modalities are used, and in which there is a need to fuse or merge the products of the two imaging modalities into a single image space.

SUMMARY OF THE INVENTION

Accordingly, the present invention is directed to the image registration of multiple medical imaging modalities using a multiple degree-of-freedom encoded fiducial device that substantially obviates one or more of the problems due to limitations and disadvantages of the related art.

An advantage of the present invention is to provide improved visualization and control during invasive surgical procedures.

Another advantage of the present invention is improved localization of surgically implanted objects in real time.

Another advantage of the present invention is to enable real time registration of multiple medical imaging modalities, whereby each modality provides images of different objects of distinct compositions in the same volume.

Another advantage of the present invention is to better enable dynamic dose calculation during radiation implant procedures, including the ability to adjust the planned implant locations to better optimize dosage as the implant progresses.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings. To achieve these and other advantages and in accordance with the purpose of the present invention, as embodied and described, a system for registering images from two medical imaging modalities comprises a first imager having a first coordinate frame; a second imager having a second coordinate frame; a fiducial having features visible to the first imager, the fiducial having a fiducial coordinate frame that has a known position and orientation relative to the second coordinate frame; and a data system.

In another aspect of the present invention, the aforementioned and other advantages are achieved by a device for registering images acquired by a plurality of medical imaging modalities. The device comprises a support structure; a first wire disposed on the support structure, the first wire substantially formed in the shape of a straight line; and a second wire disposed on the support structure, the second wire substantially formed in the shape of an ellipse.

In another aspect of the present invention, the aforementioned and other advantages are achieved by a method for registering images from a first imaging modality to a second imaging modality. The method comprises acquiring a first image from a first imager having a first coordinate frame; acquiring a second image from a second imager having a second coordinate frame; determining a first coordinate transformation between the first coordinate frame and a fiducial coordinate frame corresponding to a fiducial; and registering the first image to the second coordinate frame according to the first coordinate transformation In another aspect of the present invention, the aforementioned and other advantages are achieved by a method for reconstructing a three-dimensional structure of a plurality of objects using images acquired by a two-dimensional imager. The method comprises acquiring a first image of the plurality of objects at a first orientation; estimating a first pose corresponding to the first orientation; acquiring a second image of the plurality of objects at a second orientation; estimating a second pose corresponding to the second orientation; acquiring a third image of the plurality of objects at a third orientation; estimating a third pose corresponding to the third orientation; computing a first minimum cost correspondence between each of the seeds in the first image with each of the seeds in the second image and with each of the seeds in the third image; and computing a first minimum cost pose estimation based to the first correspondence.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

The invention provides registration of two medical imaging modalities by registering multiple images from a first imaging system, preferably at different angles, to a three-dimensional coordinate frame defined by the field of view of a second medical imaging system. The two medical imaging modalities preferably complement each other such that one imaging modality provides better quality images of certain features than the other, whereas the second imaging modality provides better quality images of other features. Registering the images from the two imaging modalities is done by determining a pose estimation, wherein the pose estimation is a six degree of freedom (six-DOF) coordinate transformation. The six-DOF transformation may be represented as a transformation matrix, or some other mathematical representation, from the coordinate frame of a fiducial, such as a fiducial device, to the coordinate frame of the field of view of the first imaging modality. The fiducial device is a six-DOF spatially encoded reference that is visible to the first imaging modality and has a known six-DOF coordinate transformation relative to the coordinate frame of the second imaging modality. Registration, as used herein, is the act of using the pose estimation and the known six-DOF transformation matrix from the coordinate frame of the fiducial device to the coordinate frame of the second imaging modality to map the image from the first imaging modality into the coordinate frame of the second imaging modality. This mapping may be done of a pixel by pixel basis. By registering the imagery provided by the two imaging modalities in such a manner, the invention provides a user, such as operating room personnel, with the capability of locating an object in three-dimensional space within the patient in real time. Examples of this capability include being able to locate radiation seeds injected into a patient's prostate while knowing the location of the seeds relative to soft tissue within and surrounding the prostate.

Figure 1:
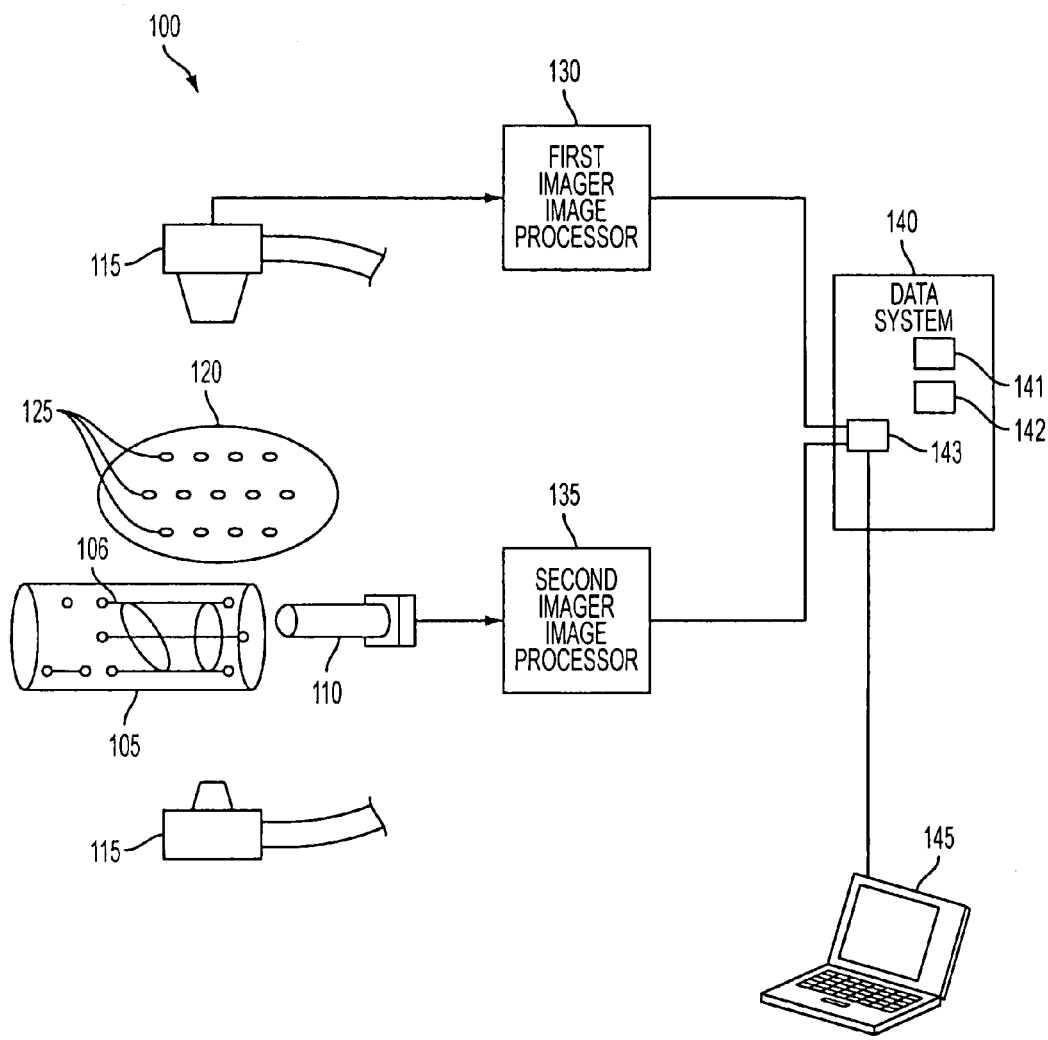
FIG. 1 illustrates a first exemplary system for registering imagery from a first imaging modality to that of a second imaging modality according to the present invention.

FIG. 1 illustrates a first exemplary system 100 for registering a first and second medical imaging modalities in a real time according to the present invention. System 100 includes a first medical imaging subsystem 115 (hereinafter "first imager"), which has a first imager image processor 130; a second imaging subsystem 110 (hereinafter "second imager"), which has a second imager image processor 135; a fiducial device 105; a data system 140, and a user interface 145.

First imager 115 and second imager 110 may be selected based on wavelength regimes (such as X-ray), electromagnetic properties (such as MRI), or acoustic properties (such as ultrasound), whereby the first imager 115 may be suited for imaging objects such as metal instruments or radioactive seeds, and second imager 110 may be suited for imaging soft tissue.

The subjects of the first imager 115 and the second imager 110 may include a region of soft tissue 120 and foreign objects 125 introduced into the soft tissue 120. Examples of soft tissue 120 may include a gland such as a prostate, or an organ. Examples of foreign objects 125 may include sensors, radioactive seeds, surgical implants, instruments such as needles or catheters, or some object or objects that have a composition different from that of the soft tissue 120.

First imager 115 may be a C-arm fluoroscope, although other transluminar projective imaging systems may be used that provide imagery from multiple angles, provided that the first imager 115 is capable of providing images of the foreign objects 125 and the fiducial device 105 with sufficient spatial resolution and quality to allow the orientation of the fiducial device 105 and the positions of the foreign objects 125 to be determined to a desired accuracy and precision. The first imager 115 may be repositioned between image acquisition. Alternatively, if the first imager 115 simultaneously provides multiple images from different fields of view, such as a first imager 115 having multiple spatially calibrated detectors, then the first imager 115 may acquire multi-angle imagery without having to be repositioned. Other examples of candidate first imagers 115 include X-ray Biplane simulators, X-ray Angiography, MV imaging, infrared telemetry, Nuclear Imaging like PET (Positron Emission Tomography). It will be readily apparent to one skilled in the art that still other medical imaging systems may be used for the first imager 115.

The second imager 110 provides images having a coordinate system to which the images from the first imager 115 are registered. The second imager 110 preferably provides images in a three-dimensional space. Second imager 110 may be a Transrectal Ultrasound (TRUS) system, although other alternate imaging systems may be used that provide a three-dimensional image to which imagery from the first imager can be registered. Other possible imaging systems for second imager 110 include computed tomography (CT), single photon emission computed tomography (SPECT), positron emission tomography (PET), kilovoltage/megavoltage (KV/MV) imaging, optical imaging, ultrasound, and MRI (Magnetic Resonance Imaging) systems. Preferably, the second imager 110 provides real time imagery of soft tissue 120. Although the second imager 110 of exemplary system 100 includes a TRUS system that is inserted into a body cavity, other systems may be used that have sensors placed outside the patient's body and which may or may not make contact with the patient's body.

The fiducial device 105 is a spatial reference designed to encode six degrees of freedom (DOF) information from a single image from any angle. Six-DOF includes three axes of translation and three angles of rotation around the respective three axes, wherein the three axes define the coordinate frame of the fiducial device 105. The fiducial device 105 has features 106 that are visible to the first imager 115. The features 106 have a specific shape and orientation, and are made of a material that is visible to the first imager 115. Encoding six DOF in an image from any angle means that the features 106, as imaged by the first imager 115, yield a unique projection or shape in the image for any given viewing angle. In other words, there is a one-to-one mapping between the projected image of the features 106 disposed on the fiducial device 105 and the viewing angle of the first imager 115.

Figure 2:
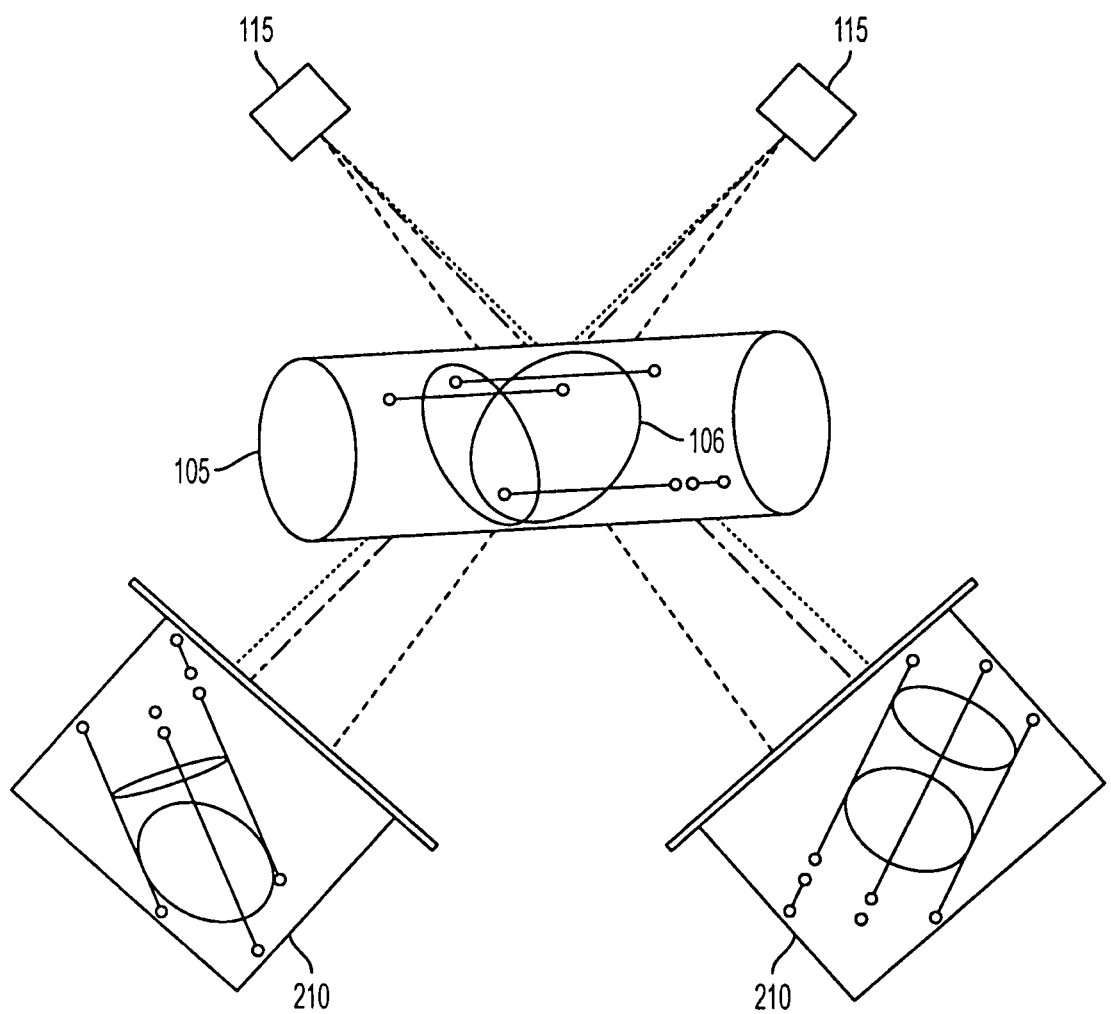
FIG. 2 shows two distinct images of a fiducial, as may be acquired by a C-arm fluoroscope at multiple angles.

FIG. 2 illustrates how the design of the features 106 disposed on the fiducial device 105 may yield a unique image depending on viewing angle of the first imager 115. Images 210 show the features 106, which are designed to be visible to the first imager 115. Each image 210 of the features 106 on the fiducial device 105, as seen by the first imager 115, shows a unique projection of the fiducial device 105 as a function of viewing angle.

The accuracy, precision, and robustness of pose estimation depends on the design and precise manufacturing of the fiducial device 105. Fiducial device 105 may have a group of features 106 such as ellipses, straight lines, and points disposed on the device. The choice of features are not limited to the above. Other exemplary features 106 may include parabolas, hyperbolas, helixes or other parametric curves.

The use of ellipses, straight lines, and points provide different advantages and disadvantages. An advantage of using a given configuration of features 106 is that it may provide for an accurate pose estimation over a wide range of orientations. In other words, the shape of the given feature may be such that there is a high probability that resulting pose estimation will be accurate. A disadvantage may be that the shape is complex and pose estimation is very computationally intensive. In short, the shape of a given feature within features 106 may provide a robust pose estimation in that it provides for a nominally accurate pose estimation for a short and consistent amount of computing time. For instance, ellipses, straight lines, and points respectively increase in order of possibility of error of 6-DOF determination, but respectively decrease in order of computational complexity. In other words, ellipses make pose estimation more accurate, while points make pose estimation more robust. In the embodiment illustrated in FIGS. 1 and 3 fiducial device 105 has features 106 that include a combination of shapes that provide a balance of such advantages and disadvantages, thereby substantially balancing accuracy and robustness.

For any feature within features 106, regardless of its shape, the accuracy of pose estimation is a function of orientation. For example, the accuracy of pose estimation using a single ellipse is greater from a viewing orientation normal to the plane defined by the ellipse, and lesser from a viewing angle parallel to the plane. Accordingly, by providing a particular combination of shapes and orientations for features 106 on fiducial device 105, fiducial device 105 may be designed such that the accuracy of a given pose estimation is consistent at different viewing angles. For instance, the orientation of features 106 should be such that with a change in first imager 115 orientation, as the orientation of one feature within features 106 in the image becomes less discernable, the orientation of another feature within features 106 should become more discernable. With such a configuration of features 106, the accuracy and precision of the six-DOF encoding of fiducial device 105 may be minimally dependent on its orientation, which means that the precision of the pose estimation is consistent regardless of the orientation of fiducial device 105. The combination of features 106 on the fiducial device 105 illustrated in FIG. 1 is exemplary, and other combinations are possible and within the scope of the invention.

Fiducial device 105 may be fixed in 6-DOF space relative to the field of view of the second imager 110, which would substantially fix the coordinate frame of the fiducial device 105 to the coordinate frame the image space of second imager 110. Optionally, fiducial device 105 may be able to move relative to the field of view of second imager 110, in which case there would need to be a way of measuring the position and orientation (six-DOF) of fiducial device 105 relative to second imager 110. Measuring the position and orientation may be accomplished by devices such as optical encoders, mechanical encoders, and the like. The six-DOF measurements made by such encoders may then be used to derive a transformation matrix from the coordinate frame of the fiducial device 105 to the coordinate frame of the second imager 110. Fiducial device 105 may be integrated with, co-located with, or located separately from the second imager 110. Fiducial device 105 may be placed within the patient, such as within a cavity, or may be placed outside the patient, provided that fiducial device 105 remains substantially fixed relative to the tissue 120 and objects 125 within the tissue.

Features 106 of fiducial device 105 may be formed out of any combination of substances that are appropriately opaque to first imager 115. For example, fiducial device 105 of exemplary system 100 includes features 106 formed of about 1 mm thick Tantalum wire. The Tantalum wire is disposed on a hollow cylinder, which serves as a support structure. Fiducial device 105 of exemplary system 100 may have dimensions such that the features 106 fit within a volume of about 3 cm×3 cm×5 cm. If first imager 115 is X-ray based, then features 106 are preferably formed of materials with good visibility under X-ray illumination, such as Tantalum. Other materials may be used in the case of an X-ray-based first imager 115, provided that the material results in a good X-ray contrast. If first imager 115 operates in a different imaging modality, then features 106 should be made of material that will provide sufficient contrast in the images of first imager 115.

Data system 140 includes at least one processor 141 for executing computer instructions associated with the present invention; a memory 142 encoded with computer instructions and configuration constants; and interface devices 143 for communicating with the first imager image processor 130, the second imager image processor 135, and the user interface 145. Processor 141 may include a single computer or may be include multiple computers that may be collocated or distributed over a wide area and networked together. Data system 140 may be integrated into either first imager image processor 130, second imager image processor 135, or distributed between both. If data system 140 is distributed between both image processors, then first imager image processor 130 and second imager image processor 135 may communicate directly with each other and the user interface 145. The user interface 145 may be collocated with the data system 140, integrated with the data system 140, or may be remotely located. If remotely located, user interface 145 may communicate with the data system 140 over the internet. It will be readily apparent to one of ordinary skill that many such architectures for data system 140 are possible.

As mentioned above, the data system 140 includes a memory 142 encoded with computer instructions and data values. The computer instructions (hereinafter the "software"), when executed by the processor 141, perform the steps to register multiple medical imaging modalities.

Figure 3:
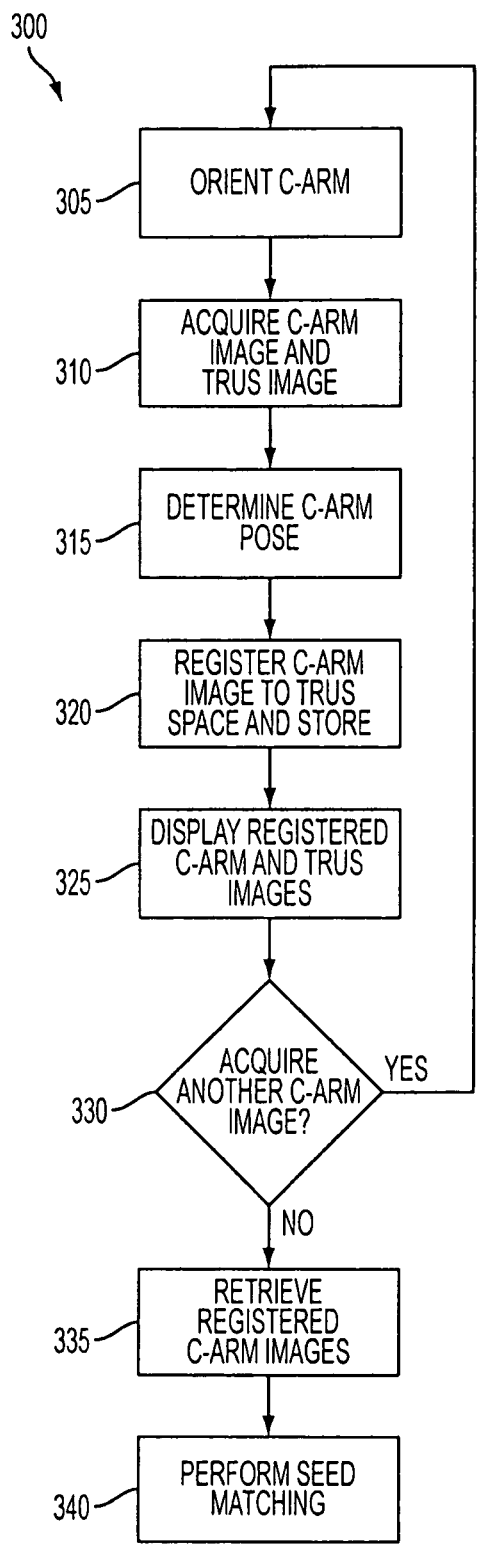
FIG. 3 illustrates an exemplary process for registering imagery from a C-arm fluoroscope to that of a TRUS imager according to the present invention.

FIG. 3 illustrates an exemplary process 300, which may be implemented all or in part by the software, for performing image registration and locating a plurality of foreign objects 125 within soft tissue 120. Exemplary process 300 may be fully automated, or it may involve operator interaction through the user interface 145. Exemplary process 300 may be used with an embodiment of exemplary system 100 in which the first imager 115 is a C-arm fluoroscope; the second imager 110 is a TRUS system; and the foreign objects 125 are brachytherapy seeds that have been injected into prostate soft tissue 120.

Exemplary process 300, as implemented using exemplary system 100, works as follows. In step 305, first imager 115 (the C-arm fluoroscope) is positioned to a first orientation relative to the fiducial device 105. This may be done manually or automatically through the software executed by the processor 141.

In step 310, first imager image processor 130 acquires fluoroscopy data from the first imager 115 and processes the data corresponding to an image. In the case in which first imager 115 is a fluoroscope and second imager 110 is a TRUS probe, the TRUS probe may be removed from the field of view of the first imager 115 to prevent interference with the image acquired by first imager 115. Data system 140 retrieves the C-arm image data from first imager image processor 130 and stores the C-arm image data values (hereinafter the "acquired C-arm image") in memory 142. Further, second image processor 135 acquires TRUS data from the second imager 110. Data system 140 retrieves the TRUS image data from second image processor 135 and stores the TRUS image data values (hereinafter the "acquired TRUS image") in memory 142.

Once data system 140 has stored the image data values, processor 141 executes the software to compute the six-DOF pose estimation of the first imager 115 in step 315. As mentioned earlier, the pose estimation is a 6-DOF representation, such as a transformation matrix, of the transformation from the coordinate frame of fiducial device 105 to the coordinate frame of first imager 115.

In step 320, data system 140 executes the software to register the acquired C-arm image (from first imager 115) to the coordinate frame of the acquired TRUS image (from second imager 110), by using the pose estimation computed in step 315, and stores the resulting data values corresponding to the registered C-arm image (hereinafter the "registered C-arm image") in memory 142. Algorithms for performing the registration of step 320 are well known to the art of image processing. It will be apparent to one skilled in the art that existing image processing software packages may be used to implement image registration in step 320, and that the use of such software packages is within the scope of the invention.

In step 325, data system 140 retrieves the registered C-arm image data values, and the acquired TRUS images, from memory 152, and sends the two images to user interface 145 to be displayed in an overlaid fashion.

In step 330, data system 140 executes the software to query the user if another registered C-arm image, from first imager 115, is desired. At least two registered C-arm images are required to perform seed matching in subsequent step 340. If the answer is affirmative, steps 305-325 may be repeated. During a second iteration of steps 305-325, a second TRUS image need not be acquired by second imager 110, if multiple C-arm images are to be registered to the coordinate frame of a single TRUS image.

In step 335, data system 140 retrieves the acquired TRUS image and the registered C-arm images from memory 142.

In step 340, data system 140 executes the software to perform seed matching, in which the seeds imaged in one registered C-arm image are matched to the corresponding seeds in other registered C-arm images. In other words, in seed matching, a given seed is identified in both registered C-arm images, and then located in the space defined by the coordinate frame of the second imager 110.

Exemplary processes for implementing step 315 are described as follows.

Figure 4:
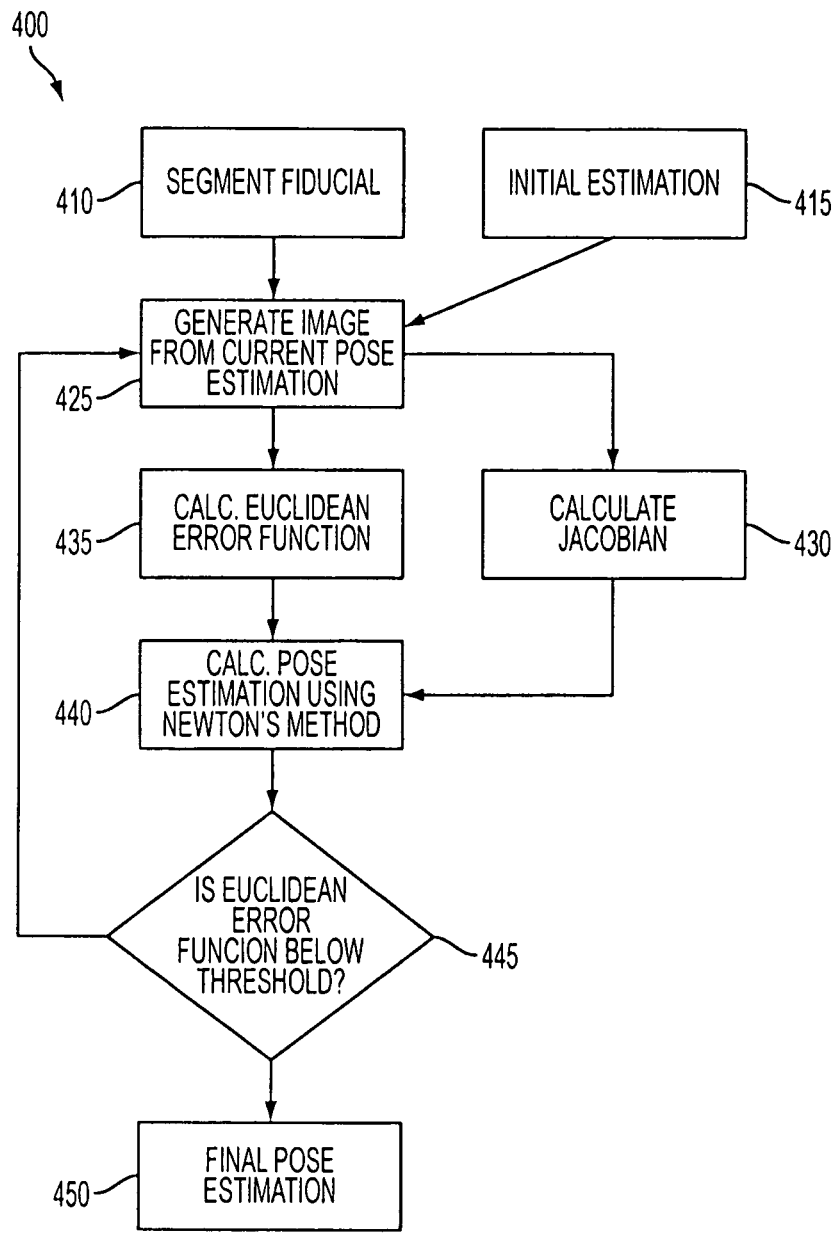
FIG. 4 illustrates an exemplary "basic" process for estimating the pose of a C-arm fluoroscope relative to a fiducial.
Figure 5:
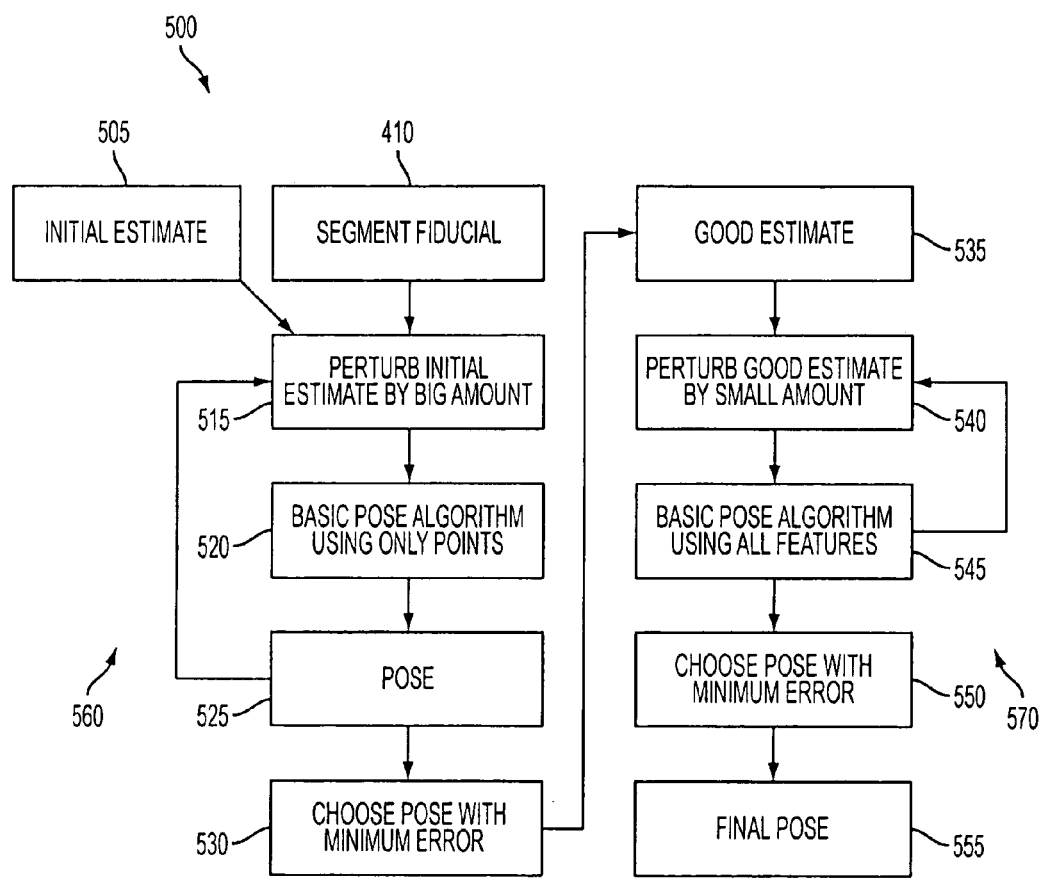
FIG. 5 illustrates an exemplary "robust" process for estimating the pose of a C-arm fluoroscope relative to a fiducial.

FIGS. 4 and 5 illustrate two exemplary implementations of step 315. FIG. 4 illustrates a "basic" pose estimation algorithm 400 that may be implemented in the software in data system 140; and FIG. 5 illustrates a "robust" pose estimation algorithm 500 that may be implemented in the software. Selection of which pose estimation algorithm to use may depend on the available computational power of data system 140 as well as pose estimation accuracy and precision requirements.

Referring to FIG. 4, "basic" algorithm 400 is an iterative process in which a pose estimation is iteratively computed until it converges on a solution that is within a pre-defined acceptable error threshold.

In step 410 of "basic" algorithm, processor 141 executes the software, which segments features 106 of fiducial device 105. To segment features 106 is to distinguish features 106 of fiducial device 105 from the background image. The software may implement any of a number of segmentation image processing algorithms that are capable of identifying those pixels that correspond to features 106 and identifying parametric curves corresponding to features 106 to sub-pixel precision. Typical segmentation methods may include thresholding followed by edge filtering and Hough Transforms. Approaches like Random Sample Consensus (RANSAC) can be used to further improve results. Various segmentation algorithms such as these are known to the art, and their use is within the scope of the invention.

The software may implement segmentation in a semi-automatic mode or an automatic mode. In semi-automatic mode, the software displays the acquired C-arm image (which shows features 106) on user interface 145. The operator then selects various points in the acquired C-arm image (for example, by clicking on it with a mouse attached to user interface 145) in a pre-set order. The selected points should be close to the shown features of interest, which are the displayed features 106 in the acquired C-arm image. The software does the following: it performs a minimum intensity centroid search in the neighborhood of each selected point, which fine-tunes the location; it performs a least square curve fitting in order to obtain the equation of the straight line and ellipse; and it projects the centroid on its corresponding straight line and ellipse to get the final position.

In automatic mode, the software implements a Hough Transform to segment the parametric curves of the corresponding to features 106 on fiducial device 105. The software achieves this by creating an edge image based on the image acquired by first imager 115, and then searching in the parametric space defined by the edge image for parametric curves, which includes straight lines and ellipses, that correspond to features 106 of fiducial device 105.

To identify straight lines, the software performs a Hough Transform. The software may then fine tune each straight line by doing the following: searching for minimum intensity points in a small neighborhood surrounding each line; running a RANSAC-based least square fitting on these points; and selecting the three strongest near-parallel straight lines. RANSAC-based line fitting includes running a filter in the neighborhood of each line and extracting a large number of possible points on the line. Some of these points may be erroneous and may corrupt the final answer, while most of the points may be good. This process may be repeated many times to pick points from the output of the Hough Transform at random, with which it fits a line. The line that repeats most often is the final correct answer.

To identify ellipses, the software may execute a Hough Transform to estimate various possible axes of symmetry in the image. To achieve this, the software performs a 2D Hough Transform to find the best ellipse for each center of axis of symmetry. The software then fine-tunes the ellipse associated with each center using an approach similar to the one used for the lines. Finally, the software selects the two strongest ellipses, which correspond to the ellipses in features 106 on fiducial device 105.

The result of the segment fiducial step 410 is a segmented projection of features 106 in the two-dimensional coordinate frame of first imager 115. The segmented projection may include a set of points in the two-dimensional coordinate frame of first imager 115, a set of lines each defined by two endpoints and parameters defining the line between the endpoints, a set of ellipses defined by a plurality of points defining a given ellipse, and a parametric equation for the ellipse defined by the points. The segmented projection may be used as an initial estimate 415 for the pose estimation.

The software then computes the pose estimation by iteratively performing steps 425-445. In step 425, the software retrieves from memory 142 the data values corresponding to the current pose estimation and parameter values corresponding to features 106. As mentioned earlier, if this is the first pass through step 425, then the current pose estimation is initial estimate 415. Then the software generates an estimated or "fake" image of features 106, which is a two-dimensional projection of the features 106 according to the current pose estimation. The software then stores the estimated image data values in memory 142. Alternatively, the process of generating an estimated or fake image may be done using Digitally Reconstructed Radiography.

In step 435, the software retrieves the data values corresponding to the C-arm image acquired by first imager 115, and the estimated or "fake" image, and computes a Euclidean distance or Euclidean error function. The Euclidean distance is a matrix containing vectors between the corresponding points, lines, and ellipses of the acquired and estimated image. The Euclidean distance $\delta x_i, \delta y_i$ is a measure of the accuracy of the pose estimation and is defined by the relation $$\delta x_i = x_i(R^i, T^i) - \bar{x}_i$$

$$\delta y_i = y_i(R^i, T^i) - \bar{y}_i$$

where $(x_i, y_i)$ are the coordinates for a given point on the estimated image, $(\bar{x}_i, \bar{y}_i)$ are the coordinates of the corresponding point on the actual image, $(R^i, T^i)$ are the respective rotational and translational components of the current pose estimation, and i corresponds to the ith iteration of steps 425-440. The above equations for the Euclidean distance $\delta x_i, \delta y_i$ are for points in the images. The Euclidean distance for two lines may be computed by computing the Euclidean distances for the respective endpoints of each line. The Euclidean distance for two ellipses may be computed using the following relation:

$$\frac{ab}{2\sqrt{a^2+b^2}} \frac{(AC - B^2/4)}{\det(M)} [\bar{x}_i \quad \bar{y}_i \quad 1] \begin{bmatrix} A & B/2 & D/2 \\ B/2 & C & E/2 \\ D/2 & E/2 & F \end{bmatrix} \begin{bmatrix} x_i \\ y_i \\ 1 \end{bmatrix}$$

where a is the major axis of the ellipse, b is the minor axis of the ellipse, $(\bar{x}_i, \bar{y}_i)$ are the coordinates of a point on the ellipse in the acquired image, $(x_i, y_i)$ are the coordinates of a point on the ellipse in the estimated image, M is shorthand for the matrix $$\begin{bmatrix} A & B/2 & D/2 \\ B/2 & C & E/2 \\ D/2 & E/2 & F \end{bmatrix}$$

and A-F are parameters defining an ellipse in the acquired image, as determined in segmentation step 410. The parameters A-F define an ellipse according to the general equation for a conic representation of an ellipse $$[x \quad y \quad 1] \begin{bmatrix} A & B/2 & D/2 \\ B/2 & C & E/2 \\ D/2 & E/2 & F \end{bmatrix} \begin{bmatrix} x \\ y \\ 1 \end{bmatrix} = 0.$$

In step 430, the software generates a Jacobian Matrix based on the current pose estimation. In general, the Jacobian Matrix corresponds to a multidimensional derivative of the current pose estimate. In an exemplary implementation, the Jacobian is a 48×6 matrix, where the "48" dimension corresponds to 9 points leading to 18 of the dimensions (x and y), 3 lines leading to 6 dimensions, 2 ellipses leading to 24 dimensions, and the "6" dimension refers to the six-DOF.

In an exemplary embodiment, the Jacobian Matrix for a given point may be a combination of translational and rotational elements:

$$J = \begin{bmatrix} \frac{\partial x_i}{\partial T_1} & \frac{\partial x_i}{\partial T_2} & \frac{\partial x_i}{\partial T_3} & \frac{\partial x_i}{\partial \phi_j} \\ \frac{\partial y_i}{\partial T_1} & \frac{\partial y_i}{\partial T_2} & \frac{\partial y_i}{\partial T_3} & \frac{\partial y_i}{\partial \phi_j} \end{bmatrix}$$

$$= \begin{bmatrix} \frac{-f}{s_x Z_i} & 0 & \frac{-fX_i}{s_x Z_i^2} & \frac{-f\left(Z_i \frac{\partial X_i}{\partial \phi_j} - X_i \frac{\partial Z_i}{\partial \phi_j}\right)}{s_x Z_i^2} \\ 0 & \frac{-f}{s_y Z_i} & \frac{-fY_i}{s_y Z_i^2} & \frac{-f\left(Z_i \frac{\partial X_i}{\partial \phi_j} - Y_i \frac{\partial Z_i}{\partial \phi_j}\right)}{s_x Z_i^2} \end{bmatrix}$$

where f is the focal length of the C-arm fluoroscope; $(s_x, s_y)$ are the respective x and y components of the C-arm fluoroscope pixel size; $(X_i, Y_i, Z_i)$ are coordinates of a given point P on the estimated fiducial image generated in step 425, $(T_1, T_2, T_3)$ are the translational elements, and $\phi$ is the rotational element.

Alternatively, the elements of the Jacobian Matrix corresponding to points, lines, and ellipses may be respectively computed according to the following relationships:

$$\frac{\partial(\delta x_i)}{\partial P_j} = \frac{\partial x_i}{\partial P_j}, \quad \frac{\partial(\delta y_i)}{\partial P_j} = \frac{\partial y_i}{\partial P_j} \text{ (point)}$$

$$\frac{\partial \delta_i}{\partial P_j} = \frac{1}{\sqrt{A^2 + B^2}} \left(A \frac{\partial x_i}{\partial P_j} + B \frac{\partial y_i}{\partial P_j}\right) \text{ (line)}$$

$$\frac{\partial \delta_i}{\partial P_j} = K((2Ax_i + By_i + D)\frac{\partial x_i}{\partial P_j} + (2Cy_i + Bx_i + E)\frac{\partial y_i}{\partial P_j}) \text{ (ellipse)}$$

where K is a scale factor $$K = \frac{ab(AC - B^2/4)}{(2\sqrt{a^2+b^2})\det(M)}.$$

The software may be designed such that the Jacobian Matrix is generated any time between the determination of the current estimate and the beginning of step 435. For example, in a multiprocessor data system 140, the Jacobian matrix and the Euclidean distance may be calculated concurrently on separate computers or processors. It will be apparent to one skilled in the art that different computing architectures may be employed to minimize the time to perform steps 425-440.

In step 440, the software computes a new pose estimation based on the current pose estimation, the Jacobian Matrix, and the Euclidean distance. Newton's method may be used to calculate the pose estimation, although other numerical optimization methods may be used, provided that the method is sufficiently robust and stable to compute a pose estimation in real time without suffering from singularities. In using Newton's method, the software implements the following equation:

$$\Delta P = \frac{\delta}{J},$$

where J is the Jacobian Matrix computed in step 430, δ is the Euclidean distance matrix computed in step 435, and ΔP is the change in translation and rotation (six-DOF) between the acquired image and the estimated image. In a particular embodiment, the software computes and stores values for ΔP, and then segregates ΔP into a translational component and a rotational component. With these values, the software computes the new pose estimation as $T_{i+1} = T_i + \Delta T_i$ (translation), and $R_{i+1} = R_i \Delta R_i$ (rotation), in which $T_{i+1}$ is the translational component of the new pose estimation, $T_i$ is the translational component of the current pose estimation, $\Delta T_i$ is the translational component of ΔP, $R_{i+1}$ is the rotational component of the new pose estimation, $R_i$ is the rotational component of the current pose estimation, and $\Delta R_i$ is the rotational component of ΔP. It may be necessary to normalize the Jacobian Matrix so that each degree of freedom has the same weight, and to normalize the Euclidean distance matrix so that each distance metric will have the same weight. Normalizing the Jacobian Matrix includes deriving a normalization matrix H that scales the parameter space without changing the least-squares solution. The matrix H may be derived through the relationship $G(JH)(H^{-1}\Delta P) = G\delta$ where G is the Euclidean distance $\delta x_i, \delta y_i$, J is the Jacobian Matrix, ΔP is the current pose estimation, and δ is the standard deviation. The matrix H can be constructed by using a parameter covariance matrix, which requires an initial estimate of the solution and the standard deviation of each parameter. The standard deviations are derived by computing statistics across each iteration of steps 425-445. For example, column scaling may be done using the most conservative estimates for the H matrix elements. Column scaling is a method known to the art, which does not use any a priori information, but requires identifiable parameters.

The matrix for normalizing the Euclidean distance matrix, G, may be computed by using a Gauss-Markov estimation, which requires a good estimate of the covariance matrix corresponding to the Euclidean distance. Another statistical approximation is to use a diagonal matrix with each entry being the reciprocal of the standard deviation of a particular element within the Euclidean distance matrix, which is one approach to make the Euclidean distance matrix a reasonable measure of the size of the least square error vector.

In step 440, the software computes the pose estimation using the normalization matrices H and G according to the following relationship $$\Delta P = H \cdot \left(\frac{G \cdot \delta}{G \cdot J \cdot H}\right).$$

The software then stores the values corresponding to the new pose estimation.

In step 445, the software compares the Euclidean distance with a pre-determined error threshold. If the Euclidean distance, which corresponds to the error in the pose estimation, is sufficiently small, the software stores the new pose estimation values as the final pose estimation. Otherwise, the software repeats the instructions associated with steps 425-440, with the new pose estimation taking the place of the current pose estimation.

The "basic" algorithm 400 illustrated in FIG. 4 is exemplary, and variations are possible. For example, once the Euclidean distance is computed in step 435, it may be compared with the pre-determined error threshold immediately. In this variation, if the Euclidean distance is below the pre-determined error threshold, the algorithm proceeds directly to step 450 without computing a new Jacobian Matrix and pose estimation.

FIG. 5 illustrates a "robust" pose estimation algorithm 500, which may be implemented in step 315 as an alternative to the "basic" algorithm illustrated 400 in FIG. 4. The "robust" algorithm 500 is a two stage iterative process, wherein a plurality of course pose estimations are computed in a first iterative sub-process 560, and the pose with the minimum error is chosen to be the input pose estimation to a second iterative sub-process 570. In the second iterative sub-process 570, a plurality of fine pose estimations are calculated, and the fine pose estimation with the least error is selected. The remaining plurality of fine pose estimations may be used to provide a quality term corresponding to variability of the final fine pose estimation.

In the "robust" pose algorithm 500, the software segments features 106 on the fiducial device 105 from the acquired image in step 410 in a manner substantially similar to step 410 of the basic algorithm 400.

In the first iterative sub-process 560, in step 515 the software perturbs the current coarse pose estimation by some large perturbation factor. If this is the first pass through the first iterative sub-process 560, the current course pose estimation may be an initial guess. Then the software computes a coarse pose estimation in step 520. The instructions executed in step 520 are substantially similar to those executed in the "basic" algorithm 400, except that only points are used from among features 106 in computing the coarse pose estimation (as opposed to using lines and ellipses). In step 525, the software stores the current coarse pose estimation values for later use and returns to step 515, wherein the software perturbs the current coarse pose estimation, and repeats the estimation process of step 520. The perturbation should be sufficiently large to provide a new current coarse pose estimation that is sufficiently distinct from the previous coarse pose estimation such that the subsequent coarse pose estimation may correspond to a distinct local minimum relative to the first coarse estimate. In an exemplary embodiment, a large perturbation involves a translation of approximately 30 cm and a rotation of any angle. In other words, the "robust" algorithm 500 includes iterative coarse estimates to assure that the resulting set of coarse pose estimates encompass all of the possible local minima in the pose estimation space. The number of iterations required for the first iterative sub-process 560 may be provided by the operator, or may be a stored parameter value within memory 142 of data system 140.

In step 530, processor 141 retrieves the values for each of the coarse pose estimations that were stored in step 525, and selects the coarse pose estimation that corresponds to the smallest Euclidean distance $\delta x_i, \delta y_i$. The selected coarse pose estimation is then used as an input to the second iterative sub-process 570.

The software now performs second iterative sub-process 570. In step 540, the software perturbs the selected coarse pose estimation by a small amount, and then uses the perturbed coarse pose estimation as the initial pose estimation for step 545. For example, a small perturbation may involve a translation of approximately 10 cm and a rotation of approximately 90 degrees. Step 545 may be substantially similar to steps 425-450 of the "basic" algorithm 400, except that the initial pose estimate is the output of step 530. It is also similar to the software implemented in step 520, except that step 545 may use some or all of the segmented features 106 of the fiducial device 105, such as the points, lines, and ellipses. The result of step 545 is a current fine pose estimation, the values of which are stored for each iteration of the second iterative process 570. The software may repeat step 540-545, where each current fine pose estimation is perturbed in step 540 to become the input to step 545.

The number of iterations of the second iterative sub-process 570 may be input by an operator through the user interface 145, or it may stored in memory 142 as a configuration parameter value.

In step 550, processor 141 retrieves the stored fine pose estimations and selects one to be the final pose estimation. For example, the software may select the fine pose estimate corresponding to the minimum Euclidean distance $\delta x_i, \delta y_i$, and calculate the average of the Euclidean distances computed for each iteration of the second iterative sub-process 570. The computed average corresponds to a quality figure, which may provide the operator with feedback regarding the precision of the registration of the fluoroscopy image from first imager 115 to the TRUS image of second imager 110. Further, the software may "remove outliers" whereby Euclidean distances that lie beyond a pre-defined uncertainty threshold are not included in the average. Also, in another exemplary embodiment, the software selectively retrieves a plurality of fine pose estimations and their corresponding Euclidean distances, and calculates a weighted average of the selected fine pose estimations, wherein the respective Euclidean distance corresponds to a weighting factor or coefficient for the weighted average. It will be apparent to one skilled in the art that many algorithms for selection, outlier removal, interpolation, and/or estimation may be implemented for selecting the fine pose estimation, all of which are within the scope of the invention.

Returning to exemplary process 300, regardless of whether the "basic" pose algorithm 400 or the "robust" pose algorithm 500 is used in step 315, the result of step 315 includes stored values corresponding to a pose estimation, which may be used to transform the image of the features 106 on the fiducial device 105 according to six-DOF from the coordinate frame of first imager 115 to the coordinate frame of fiducial device 105.

In step 320, the software registers the image from the first imager 115 to the image of the second imager 110. If fiducial device 105 is fixed in position and orientation relative to second imager 110, then this may be accomplished by the software, which transforms the entire (C-arm) image acquired by the first imager 115 into the coordinate frame of second imager 110. However, there may be an intermediate transformation matrix between the coordinate frame of fiducial device 105 to that of second imager 110. If fiducial device 105 and second imager 110 are fixed relative to each other, the intermediate transformation matrix may be constant, the values for which may be stored in the memory 142 of data system 140 as calibration data. However, second imager 110 may move relative to fiducial device 105. In this case, the intermediate six-DOF transformation matrix may change dynamically, and its values (position and orientation) will have to be measured. The position and orientation of second imager 110 (the TRUS imager) relative to fiducial device 105 may be measured by various encoding mechanisms such as optical encoders. Data system 140 may periodically retrieve these position and orientation measurements and store the corresponding values in memory 142. One skilled in the art will readily recognize how to implement an intermediate transformation matrix in the software.

Accordingly, the result of step 320 includes the image from first imager 115 (C-arm) and an image from second imager 110 (TRUS) registered in a single coordinate frame corresponding to the three-dimensional field of view of second imager 110. The software then displays the C-arm fluoroscopy image from first imager 115 superimposed over the TRUS image inform second imager 110 in accordance with step 325, showing what is visible to both imaging modalities within the field of view of second imager 110.

Exemplary process 300 may repeat steps 305-330 in order to register an additional C-arm fluoroscope image from first imager 115 to the coordinate frame of second (TRUS) imager 110. In this case, it would be preferable to have the next C-arm image from first imager 115 be from a different orientation relative to the previous C-arm image, so that features such as foreign objects 125 may be more easily located in the three-dimensional TRUS coordinate frame of second imager 110. For example, in a first iteration of step 305, first imager 115 (C-arm) may be reoriented into a position that may advantageously provide images of the foreign objects 125 in the surrounding soft tissue 120. It may be preferable to reorient first imager 115 such that the subsequent first imager 115 image coordinate frame is substantially orthogonal to the previous first imager 115 coordinate frame. A preferable juxtaposition of first imager 115 for subsequent image acquisitions may depend on the nature of the subject and the medical procedure being performed. If the C-arm, or any imager being used for first imager 115, has multiple detectors and multiple fields of view, it may be possible to simultaneously acquire multiple images from first imager 115 at multiple image coordinate frames. Exemplary process 300 may be compatible with simultaneous multiangle imaging. In this case, first imager 115 would only need to be oriented once.

Subsequent iteration of steps 305-330 may be performed in a manner substantially similar to the above description for those steps. At the completion of step 330, the desired number of C-arm images from first imager 115 have been acquired, registered according to their own unique orientation, and stored. Again, FIG. 2 illustrates two images 210 of features 106 on fiducial device 105 acquired by first imager 115 at multiple angles. As illustrated, each image is at a different orientation, and each provides a unique image of features 106.

Figure 6A:
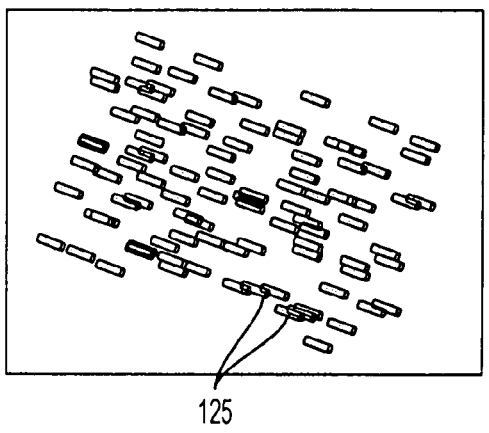
FIGS. 6A and 6B show a field of brachytherapy seeds as acquired by a C-arm fluoroscope at multiple angles.
Figure 6B:
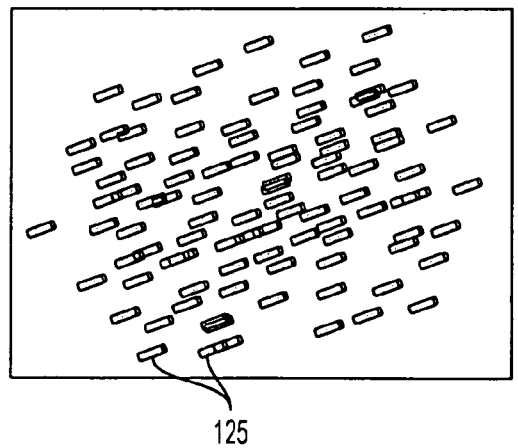

FIGS. 6A and 6B show two different C-arm fluoroscopy images of a field of seeds 125 acquired at different viewing angles. The images shown in FIGS. 6A and 6B are exemplary of two images acquired and stored in exemplary process 200, except that the features 106 of the fiducial device 105 are not shown.

Figure 7:
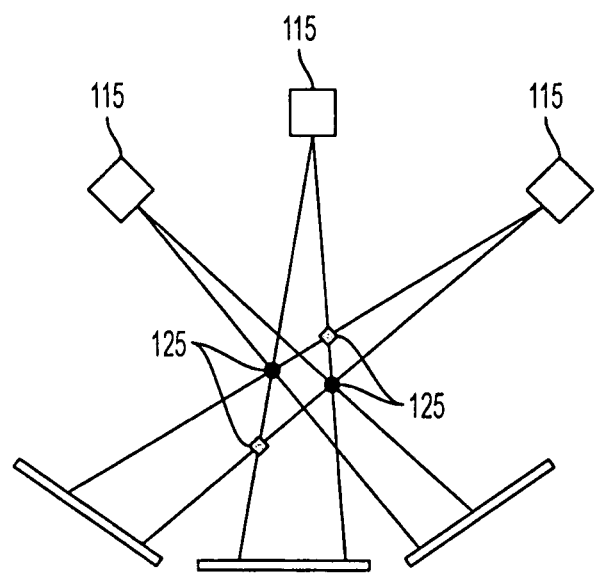
FIG. 7 illustrates multiple C-arm fluoroscope fields of view capturing a single field of brachytherapy seeds from multiple viewing angles.

FIG. 7 illustrates a field of four seeds 125, all of which are within the fields of view of multiple orientations of first imager 115. The combination of unique orientations of the field of seeds 125, as projected within the fields of view of first imager 115 at different viewing angles, enables the use of one of several algorithms to match and locate the seeds.

Returning to process 300, seed matching is performed in step 340.

Figure 8:
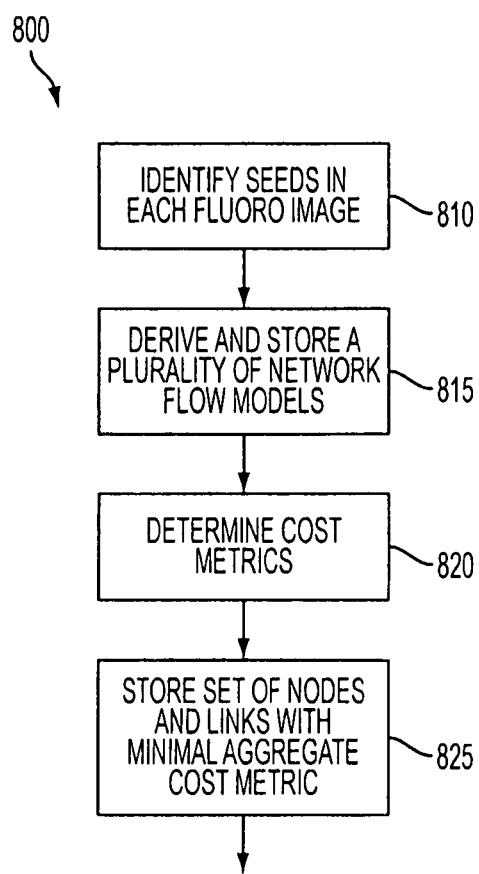
FIG. 8 illustrates an exemplary process for matching brachytherapy seeds in multiple registered images according to the present invention.

FIG. 8 illustrates an exemplary process 800 for matching seeds in step 340. As mentioned earlier, each seed is a small radiation implant that is injected into a prostate for medical procedures such as cancer treatment. By knowing the location of each seed in relation to the prostate, it is possible to more accurately deliver a radiation dose to the prostate, and more precisely estimate the radiation dose delivered.

In step 810, the software performs one of a number of known image processing algorithms to identify and locate the seeds in each C-arm fluoroscopy image from first imager 115. This results in a plurality of sets of coordinates in the TRUS coordinate frame of second imager 110: one set per C-arm image from first imager 115, and one coordinate per seed. For a given set of seeds, each seed having been extracted from each C-arm fluoroscopy image, the software assigns a network flow. In assigning a network flow, the software assigns a node to each seed identified in each C-arm image and assigns a unique plurality of links between each node in one of the C-arm images with a plurality of nodes in the other C-arm images. The plurality of links between the nodes of each C-arm image represents the possible matching of seeds between the C-arm images. The network flow may link nodes of multiple C-arm images. Nodes associated with three C-arm images may be networked accordingly. The result of step 815 includes a set of links covering all possible combinations of seeds.

In step 820, processor 141 executes the software to compute the "cost metric" of each link in the network. The cost metric refers to the length of a link between nodes. Each possible matching of seeds has an aggregate cost metric, wherein the aggregate corresponds to the sum of the links between the nodes. The correct matching of seeds is that which has the least aggregate cost metric. The software may compute a cost metric for a given link by computing the least square 3D position of the node such that the projected image coordinate of this node exhibits the least deviation from its observed locations in the various images. It will be apparent to one skilled in the art that other approaches to computing the cost of a link are possible and within the scope of the invention. For example, existing algorithms for computing minimum-cost network flow include Primal-dual algorithms for solving minimum-cost flow problems.

In step 825, the software stores the matching of seeds with the minimal cost metric in memory 142. The stored values include an identifier for a given seed and the 3-D coordinate for that seed. The result of this approach is a set of matched seeds that are identified across multiple C-arm fluoroscopy images from first imager 115. Seed matching, as performed in steps 810-825, may be done in real time or near real time.

An alternative to the network flow of process 800 is to use the Hungarian algorithm, which employs an assignment-problem-based approach, also known as the minimum weight bipartite matching problem. The Hungarian algorithm addresses the minimum-cost flow problem for two C-arm images using a N×N cost matrix of identified seeds as input. The dimension N pertains to the number of seeds identified in the two C-arm images. Implementations of the Hungarian algorithm are known to the art.

Exemplary process 800 described above may also be used to identify a particular seed shape in addition to its location. Many seeds used in medical procedures addressed by the present invention have varying geometrical features. The software may use the network flow implementation described above to determine the shape of the seed by incorporating known information regarding the seed's geometry. The software may use the geometry in computing the cost metric by assigning a node to each of the endpoints as using the known seed parameters in evaluating the cost metric associated with the seed. For example, if the seeds are cylindrical in shape, the software may incorporate the endpoint locations information along with information regarding the length of the seed. Accordingly, the cost computation function will use both the end points of each seed and its length in three dimensions to evaluate the cost metric. Thus the process 800 may be fine-tuned to identify seeds of a specific shape.

Variations to the above exemplary embodiments are possible and within the scope of the present invention. For example, fiducial device 105 may be moved within the six-DOF space of second imager 110 while the first imager 115 is left static. In this case, the movement of fiducial device 105 may be tracked by using imagery from first imager 115. By determining the locations of features 106 of the fiducial device 105 in six-DOF space relative to an anatomical feature of interest, and repeating this for multiple positions of fiducial device 105, it may be possible to determine the relative distances and orientations of (anatomical) objects in the six-DOF space. Surgical tools may be tracked using a similar technique. This may also be useful in applications such as tracking surgical tools.

In another variation, fiducial device 105 may be mounted on a robotic device (or any mobile/encoded mechanical actuator), in which the position and orientation of fiducial device 105 in six-DOF space can be registered to the coordinate frame of first imager 115, which in turn may be registered to the coordinate frame of second imager 110.

Fiducial device 105 may also serve the additional purpose of online calibration for first imager 115, wherein the need for preoperative calibration can be alleviated either partially or completely using one or more images of fiducial device 105 from either a single or multiple pose of first imager 115. Since the geometry of features 106 on fiducial device 105 are known, any distortions in the image of features 106 provided by first imager 115 may be artifacts of spatial distortion created by first imager 115. By characterizing and compensating for spatial distortion in the images of the features 106, it is possible to provide operating room personnel with imagery from first imager 115 in which spatial distortion is substantially mitigated. The products of this calibration procedure may include both the imager's spatial imaging parameters, which are generally constant, as well as variable distortion effects, which are dynamic. Accordingly, fiducial device 105 may be used for spatial calibration in a preoperative manner, in a real time manner, or both.

Although the exemplary embodiment of the present invention involves an application in radiation treatment of a prostate, other applications may include angiographic reconstruction of catheters and/or blood vessels. It will be readily apparent to one skilled in the art that many such applications are possible and within the scope of the invention.

In a variation to exemplary processes 400 and 500, steps 410 (segmentation) and 425 (current pose estimation) may be iterated within the respective overall processes. Iteratively performing segmentation and pose estimation may not only improve accuracy but may also reduce the required accuracy of the segmentation step. This is because segmentation and pose estimation have an inherent duality, i.e. knowing one directly relates to the other. Accordingly, iteratively running steps 410 and 425 may improve the accuracy of the segmentation and the current pose estimation with each pass. This may reduce or eliminate the need to have an accurate initial segmentation.

Figure 9:
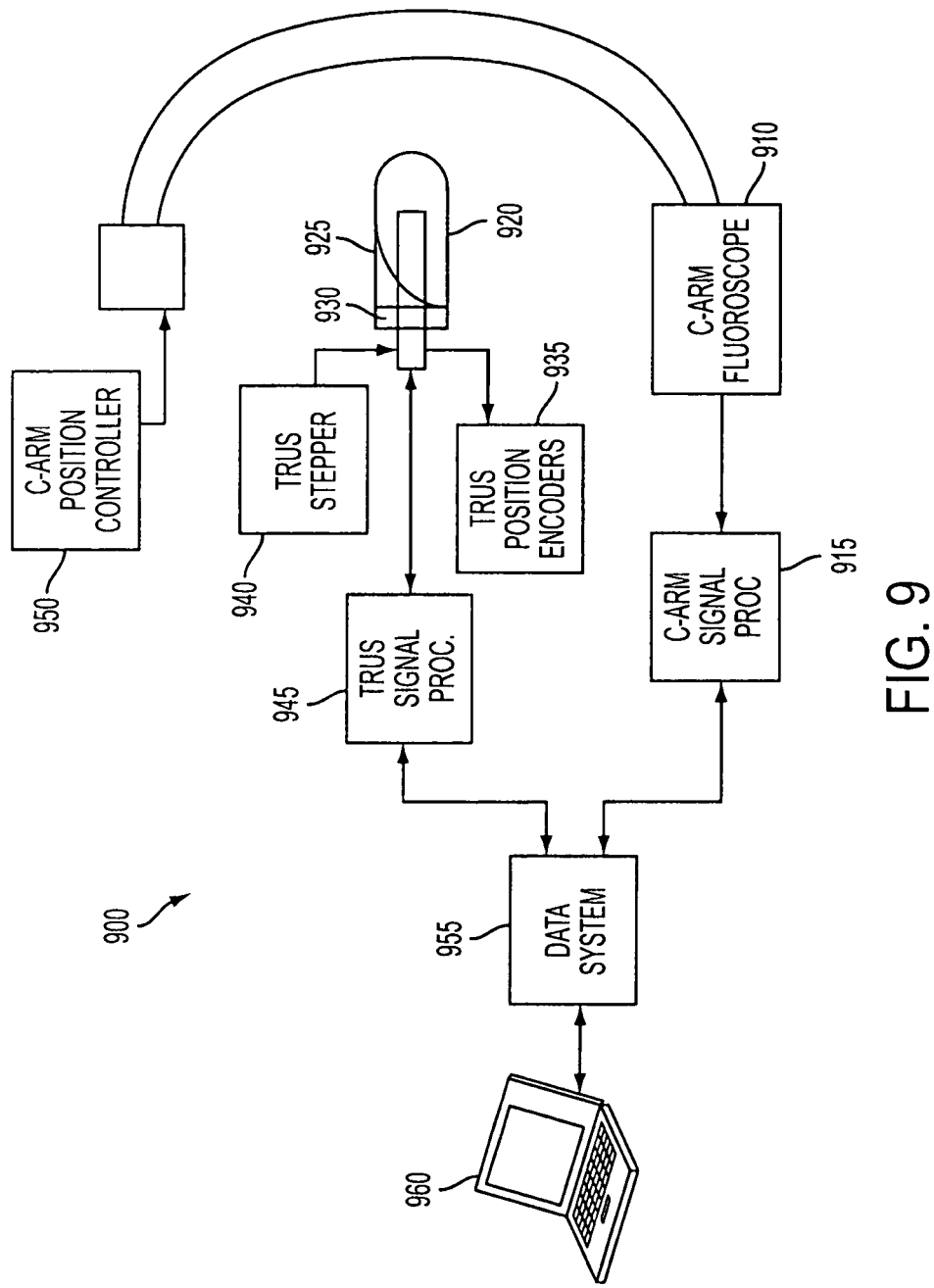
FIG. 9 illustrates a second exemplary system for registering C-arm fluoroscope images to TRUS images according to the present invention.

FIG. 9 shows a second exemplary system 900 for registering ultrasound images and C-arm fluoroscope images according to the present invention. System 900 may include commercially available TRUS and C-arm fluoroscopy hardware. System 900 includes a C-arm fluoroscope 910; a C-arm fluoroscope signal processor 915; a C-arm position controller 950; a transrectal sheath 920; a fiducial 925 disposed on the sheath; a TRUS probe 930; a TRUS stepper 940; a TRUS probe position encoder 935; a TRUS signal processor 945; a data system 955; and a computer 960, which stores and executes software for implementing processes associated with the present invention on data system 955. The computer 960 may include multiple computers, including remote databases and embedded processors. It will be apparent to one skilled in the art that data system 955 and computer 960, may be provided in many different configurations.

Figure 10:
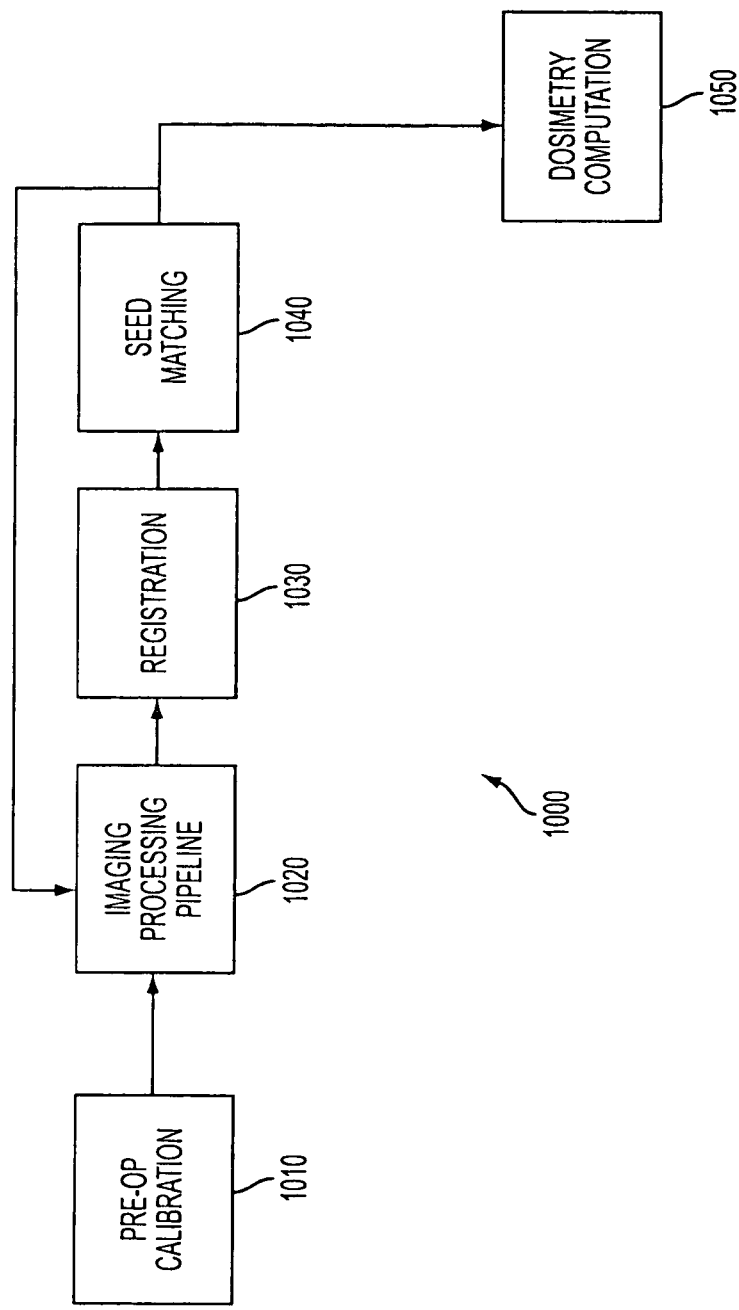
FIG. 10 illustrates an exemplary process for registering ultrasound and fluoroscopy according to the present invention.
Figure 11:
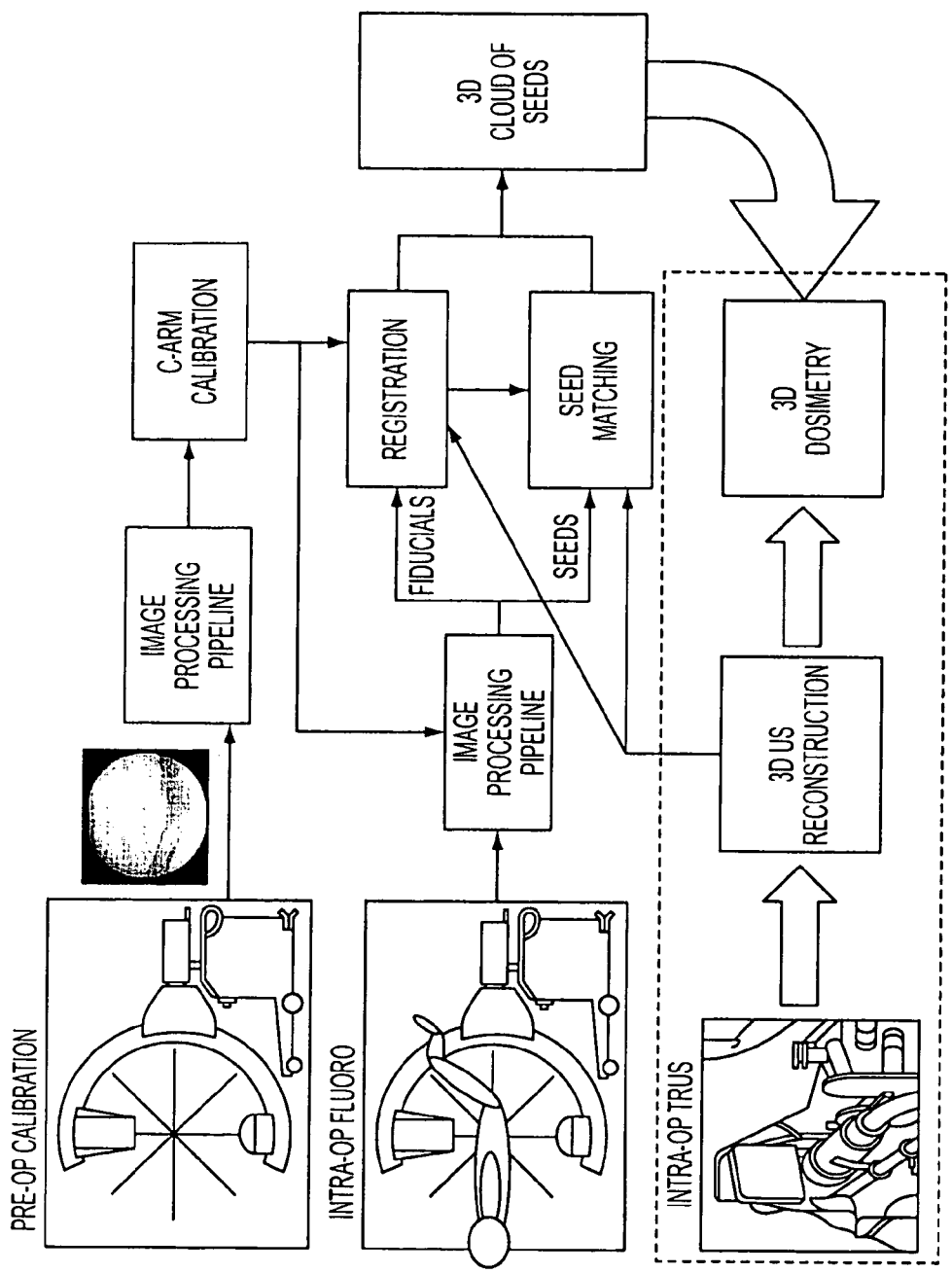
FIG. 11 is another illustration of an exemplary process for registering ultrasound and fluoroscopy according to the present invention.

FIG. 10 shows an exemplary process 1000 for registering ultrasound images and C-arm fluoroscope images according to the present invention. The process 1000 includes a C-arm fluoroscope pre-operation calibration step 1010; an image processing step (or image processing pipeline) 1020; a registration step 1030; a seed matching step 1040; and a dosimetry computation step 1050. Relevant aspects of the process 1000 are consistent with the use of C-arm fluoroscope 910 in current clinical protocols.

During pre-operative calibration step 1010, calibration fixtures (X-ray fiducials) are attached to C-arm fluoroscope 910, and images acquired by C-arm fluoroscope 910 are processed by software running on data system 955. The software then computes intrinsic spatial parameters of C-arm fluoroscope 955.

Intra-operatively, system 900 uses C-arm fluoroscope 910 to acquire images of a prostate. The software then processes the images in a manner similar to the processes used to compute the intrinsic spatial parameters. However, the software uses the intrinsic spatial parameters generated in step 1010 to produce spatially calibrated imagery. In doing so, the software may implement the same or similar processes and operations as those of image processing pipeline step 1020.

Calibration of C-arm fluoroscope 910 in step 1010 may be performed pre-operatively, before the patient is brought into the room. Commercially available C-arms fluoroscopes generally apply an electronic image intensifier, in which "parameter shift" may occur unexpectedly. Therefore it is recommend that calibration step 1010 be performed before each procedure, even if the same C-arm fluoroscope 910 is being used. It is assumed that intrinsic spatial parameters computed in step 1010 do not change during a single procedure.

Figure 12A:
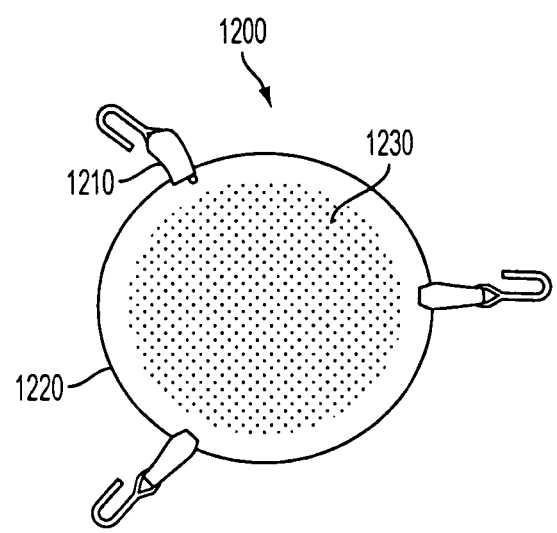
FIG. 12a shows an exemplary fluoroscope dewarping kit as may be used in the present invention.
Figure 12B:
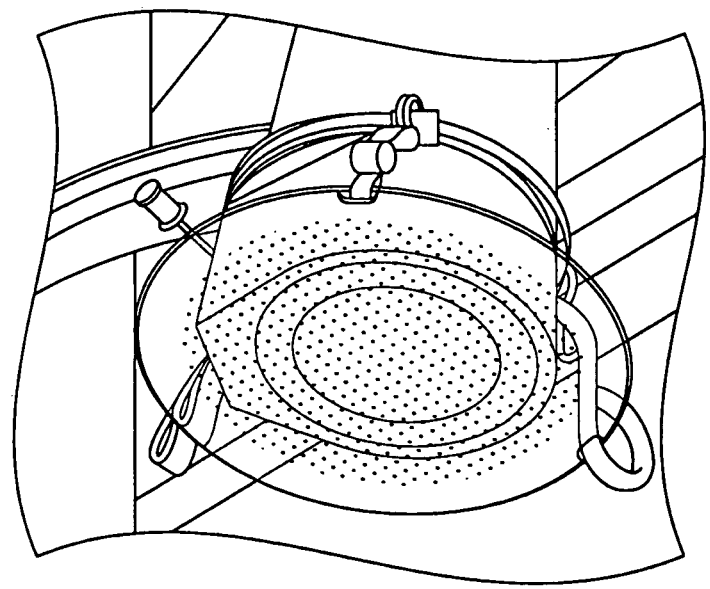
FIG. 12b shows an exemplary dewarping kit installed on a C-arm fluoroscope.

Referring to FIGS. 12a and 12b during calibration step 1010, a dewarping grid 1200 is placed on the detector of C-arm fluoroscope 910 and C-arm signal processor 915 processes the images in a set of poses in a transverse and sagittal sweep planes at approximately +30°, 0°, −30° poses. Next, the calibration step 1010 uses an image processing pipeline substantially similar to that described for step 1020, only without using the dewarping that is computed during calibration step 1010. In step 1010, the software running on data system 955 assigns labels to the beads of the dewarping grid 1200 automatically and derives a dewarping filter function. Next, a calibration object may be placed in the field, and the C-arm fluoroscope 910 is driven through the same poses as before. This time, however, the software running on data system software 955 processes the images through the complete pipeline like that of image processing pipeline step 1020, now including dewarping. The software labels the calibration fixture automatically and then calculates the intrinsic spatial parameters of C-arm fluoroscope using techniques known in the related art.

FIG. 12a shows a dewarping grid structure 1200 that may universally fit C-fluoroscopes of different detector sizes. An adjustable band clamp 910 goes around the C-arm fluoroscope 910, so that the plate 1220 hooks into blocks positioned around the C-arm, as shown in FIG. 12b. The plate 1220 is firmly attached to image intensifier and substantially does not move during the calibration process 1010. The dewarping process of image processing pipeline step 1020 does not require that the centers of the dewarping plate 920 and the intensifier be aligned. The radio-opaque beads 1230 may be arranged in triangular pattern. The dewarping algorithm implemented by the software running on data system 955 includes three basic steps: (1) establish a correlation between points in the image and points in the known bead pattern 1230 by using a fast crawling method that can circumvent problems caused by missing beads 1230 in the image, (2) determine the rigid body transformation and scale factor that will align the images, by using a conventional singular value decomposition method; and (3) align the images and perform least-squares polynomial fit between the point sets. The software may use nth-order Berstein polynomials to describe the patterns in the dewarping grid and then achieve deformable matching between warped and warp-free features.

In step 1020, the software running on data system 955 acquires images from C-arm fluoroscope 910. The software then delineates and identifies objects (seeds, needles, fiducials, etc.) in the fluoroscopic images. In doing so, image processing step 1020, includes a chain of operations acting on the X-ray images acquired by C-arm fluoroscope 910: image acquisition; dewarping; noise reduction; image normalization; background removal; thresholding; and pre-labeling.

In acquiring images from C-arm fluoroscope 910, C-arm signal processor 915 may use hardware integral to fluoroscope C-arm 910. C-arm signal processor 915 may output digital signals or produce a VHS signal that can be captured through a frame grabbing card on the computer 960. An exemplary frame grabber card includes a Matrox frame grabber, although others may be used.

The dewarping operation helps remove the spatial distortion introduced by the image intensifier of the C-arm signal processor 915. The present invention includes a dewarping fixture and corresponding computer instructions in the data system software 955, which are described later.

In the noise reduction operation, X-ray images acquired by C-arm fluoroscope 910 may be averaged over multiple frames taken with C-arm fluoroscope 910 in a single position. While this method substantially preserves image features, it also may increase radiation dose from C-arm fluoroscope 910. For example, averaging five short-burst fluoroscopy image frames may give excellent noise suppression, while exposing the patient to a dose of one radiograph.

The image normalization operation includes the act of normalizing the image for different attenuation rates corresponding to different objects in an image. The intensity of X-ray energy falls exponentially as the ray passes through the body, and the gray level of objects depends very heavily on the thickness of other objects that the ray had to penetrate on its way. Logarithmic normalization of the image may result in simple sum of the respective attenuations of the seeds and body. As the implanted seeds, needles, and fiducials tend to have large attenuation compared to bone and soft tissues, they may stand out brightly in logarithmic image.

The background removal operation is important to the accuracy of the exemplary process 1000 and its ability to find the centers and centerlines of objects in the X-ray imagery. Calculating a simple weighted centroid may not suffice, because non-point like regions may skew the determination of the center and centerline along the gray level gradient. An exemplary approach to the background removal operation may include applying a linear gradient correction followed by Gaussian filtering over a logarithmic normalized image. This approach may be used for implanted spherical markers and further expand the method for line objects and seeds. The background removal operation may use a mathematical morphology approach known in the related art for fluoroscopic imaging of prostate implants by defining a chain of four basic morphological operations: erosion, dilatation, opening, and closing.

The thresholding operation may not be done statically, because the intensity of seeds and objects also depends on the thickness of bone structures. However, the optimal threshold may be found automatically by applying entropy maximization over a two-dimensional histogram that reflects both the gray levels and spatial relationship of pixels.

The pre-labeling operation is performed to delineate and identify all objects other than seeds, then digitally remove those from the images. For example, the software running on data system 955 may use prior shape information about the objects in the field of view. Two sorts of dense objects may be expected in the field of view: implanted markers (needles, wire markers, spherical markers), and brachytherapy seeds. Needles and wire markers typically appear as thin lines that are typically well segmentable by a Hough transform implementation. At any given time, only a very limited number of marker objects are generally present in an X-ray field. Knowing the shape, orientation, and estimated relative positions of these objects, the data system software 955 may label them automatically, or with minimal input from the operator. If they are labeled once, the data system software 955 may remember where they are supposed to show up the next time and how they actually look in the images. After a marker object is positively identified, the data system software 955 calculates its 3D locations for registration purposes and then digitally removes its silhouettes from the X-ray images. This process may be repeated until only seeds are left in the images that then undergo a pattern recognition process (seed matching) described below. It should be noted that some seeds may have been obscured by marker objects and thus inadvertently removed from the images.

The result of the above operations within image processing pipeline step 1020 includes a distortion-free binary image, in which only artificial implanted objects are present, while all details of the natural body (bone, ligaments, etc.) are removed from the picture. Subsequent labeling can be further assisted by optimizing material density of the custom-made objects (de-warp grid, calibration phantom, rectal sheath, fiducials, etc.) so that the processing pipeline step 1020 can be fine-tuned to suppress or enhance these objects selectively.

In registration step 1030, the software running on data system 955 cinoytes a sux-DOF transformation between the coordinate frame of C-arm fluoroscope 910 and the coordinate frame of TRUS probe 930. In step 1030, fiducial 925 is used as a reference that can be seen by both C-arm fluoroscope 910 and TRUS probe 930 and is substantially stationary with respect to the prostate during process 1000.

Figure 13:
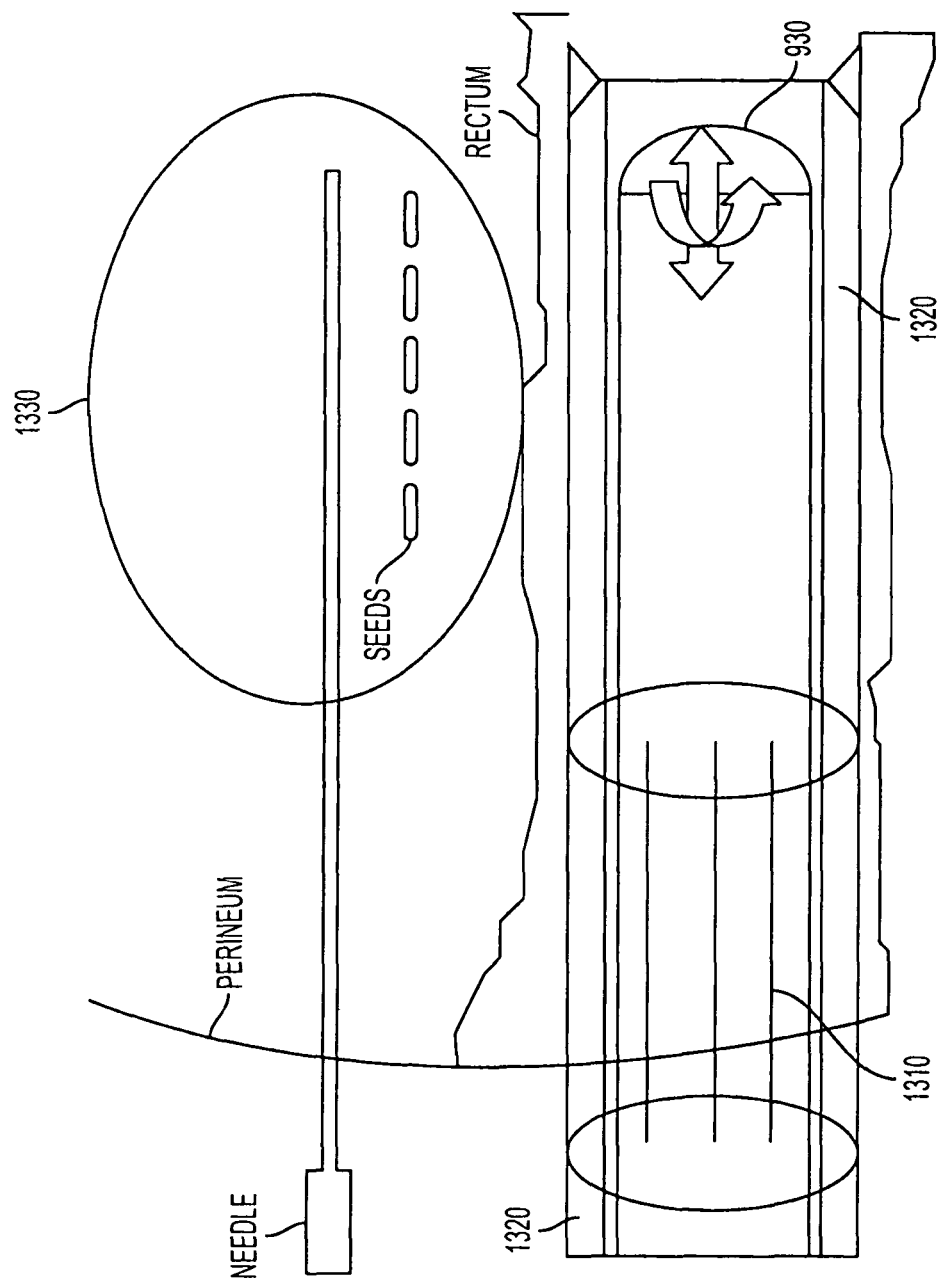
FIG. 13 illustrates an exemplary transrectal sheath, along with an ultrasound probe, as may be used in the present invention.
Figure 14:
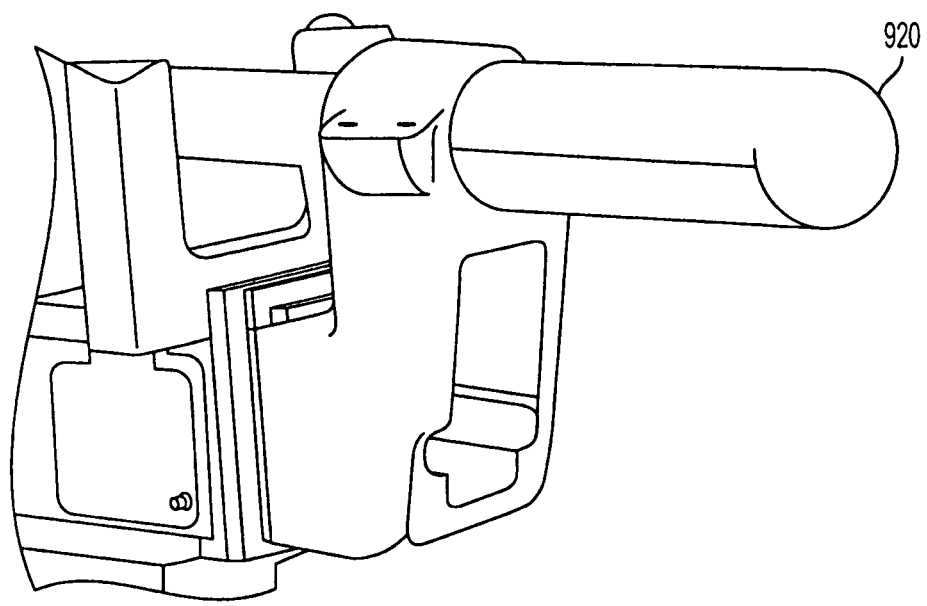
FIG. 14 shows an exemplary transrectal sheath mounted to a TRUS stepper base.

Referring to FIGS. 13 and 14, the fiducial 925 may be coupled to the coordinate frame of the TRUS probe 930 in many ways. An exemplary method can use a sheath 1320, either complete or partial, either inside or outside the patient's body. In the event of using transcutaneous ultrasound, fiducial 925 could be mounted elsewhere. Sheath 1320 could be used in addition to the mount to which fiducial 925 is attached. An exemplary transrectal sheath 920 includes six-DOF external fiducial pattern 1310 mounted on the outside of the sheath 1320, that is mounted on the base of the TRUS stepper 940 of system 900. Inside sheath 1320 the TRUS probe 930 can move freely without mechanical interaction with the rectum, thus the location and shape of the prostate 1330 does not change due to scanning motion of TRUS probe 930. Sheath 1320 may be made of thin plastic, mylar, polypropylene, polyethylene or similar material and may fit tightly round the TRUS probe 930.

Figure 15A:
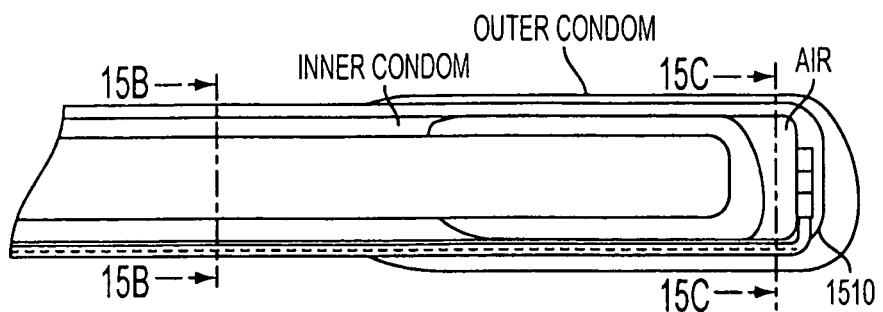
FIG. 15 is cutaway view of a transrectal sheath, a TRUS probe, acoustically coupled according to the present invention.
Figure 15B:
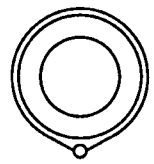
Figure 15C:
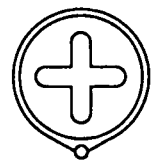
Figure 16:
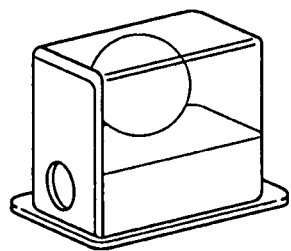
FIG. 16 shows a prostate phantom that may be used in a pre-op calibration step of the present invention.

As illustrated in FIG. 15, gel material 1510 substantially provides ultrasonic coupling between the sheath 1320 and the rectum wall. The presence of the sheath 1320 may cause some degradation of the acoustic signal, although minimizing the thickness of the sheath and maintaining even distribution of the coupling gel 1510 mitigates this effect.

Figure 17A:
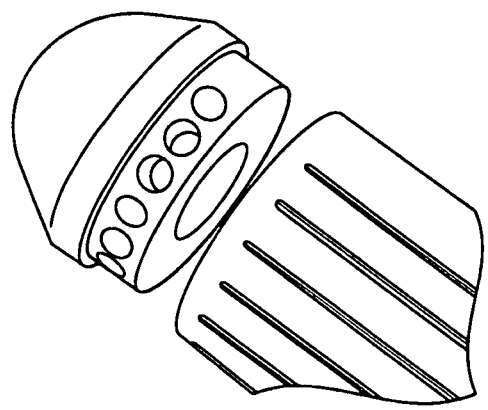
FIG. 17 shows an exemplary transrectal sheath, which includes air channels, an X-ray fiducial, and an acoustic fiducial.
Figure 17B:
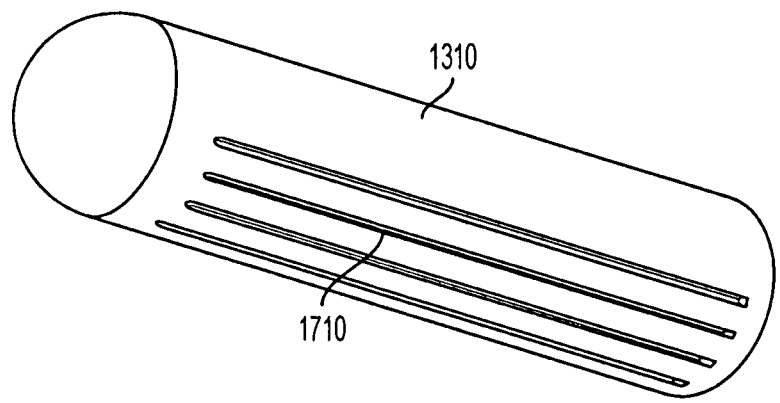

As illustrated in FIG. 17, multiple air channels 1710 substantially provide equalized air pressure in the sheath 1320 during scanning motion of the TRUS probe 930.

Fiducial pattern 1310 on the outer surface of the sheath 1320 may contain a suitable combination of straight lines, helixes, and ellipses formed using an opaque substance, as illustrated in FIG. 17. In order to determine the location of fiducials 1310 in the coordinate frame of C-arm fluoroscope 910, the relative pose of the C-arm images must be known. Fiducial pattern 1310, which is preferably precision-machined, may be rigidly fixed within the field of view of C-arm fluoroscope 910 to assist in the determination of the relative pose of the multiple images acquired by C-arm fluoroscope 910.

Fiducials pattern 1310 on sheath 1320 provides a common coordinate system for the individual X-ray images acquired by C-arm fluoroscope 910. Further, sheath 1320 may be rigidly mounted on the base of TRUS stepper 940, and the motion of TRUS probe 930 may be encoded relative to the base of TRUS stepper 940, so there is a known spatial relationship between the TRUS probe 930 and fiducial pattern 1310 at any time. Therefore, fiducial pattern 1310 on sheath 1320 provides a common reference coordinate system for both X-ray and the TRUS images. This frame of reference may be considered to be sufficiently stationary with respect to the prostate during a registration session typically involving the acquisition of multiple X-ray shots and a TRUS volume. Fiducial pattern 1310 can be auto-segmented.

In seed matching step 1040, the software running on data system 955 matches the radioactive seeds across multiple registered X-ray images acquired by C-arm fluoroscope 910. Reconstructing implanted seeds may be complicated by a large number of seeds (sometimes as many as 150) confined in a small volume, overlapping one another in an apparent disorder. The X-ray images may also be very noisy, especially in the lateral direction where the pelvic and femur bones create a strong heterogeneous shadow over the seeds. Accordingly, it is suggested that three X-ray images be acquired by C-arm fluoroscope 910. In addition, the apriori information on the inserted seeds can be used to help the technician position C-arm fluoroscope 910 to acquire images.

The software running on data system 955 may include instructions to implement a technique that draws heavily on prior information from TRUS-based implant plan (according to the surgeon's specifications) and from earlier seed matching and reconstruction sessions. Having established 3D registration between the respective coordinate frames of C-arm fluoroscope 910 and TRUS probe 930 in step 1030, the software may transfer spatially registered information from the coordinate frame of TRUS probe 930 to the coordinate frame of C-arm fluoroscope 910 to assist seed segmentation and matching in step 1040 information from the TRUS space to X-ray space to assist seed segmentation and matching, by recognizing previously reconstructed seeds. The software may implement several methods for doing this.

Certain commercially available TRUS-based treatment planning systems, such as Interplant® made by CMS Burdette Medical Systems of Urbana-Champaign, Ill., have the capability of spatially locating an inserted needle. Although there is some tissue deformation, a good estimation is provided regarding where the seeds will end up in the prostate. By projecting the location of the needle forward onto the 2D X-ray pictures, a reasonably confined area may be defined where these new seeds are supposed to show up in X-ray. Consequently, the software running on data system 955 can label clusters of previously implanted old seeds that could not have come from the newly implanted needles. The software may update the 3D locations of old seeds and then excludes those from seed matching step 1040. When a needle is retracted from the prostate, it leaves the seeds behind along a slightly bent trajectory. Based on observations of actual implants, the bending and perturbation of seeds from the ideal curvilinear trajectory may be statistically modeled by the software funning on data system 955. Using this estimate in confining the newly implanted seeds can improve the efficacy of elimination of false candidates.

It may be assumed that seeds implanted by a previous fluoroscopy session have not migrated substantially within the prostate since then. By projecting the location of these previously located seeds forward onto the 2D X-ray pictures, the software running on data system 955 can obtain a reasonably confined area where they are supposed to show up in the new X-ray images, then update their 3D locations and exclude those from seed matching step 1040, as described above.

If the prostate did not move between imaging sessions, then by subtracting the previous image from the new image taken by C-arm fluoroscope 910 in a single pose may show the newly derived seed locations and nothing else. In reality, the prostate moves somewhat between imaging sessions, and a pose of C-arm fluoroscope 910 is generally not precisely repeatable. A large portion of previously implanted seeds can be excluded from the matching problem on this basis. The software can apply the images in processing pipeline step 1020 and perform deformable mapping using information that is mutual between the images.

After seed matching step 1040 is complete, the software running on data system 955 may transform the location of seeds to the coordinate frame of TRUS probe 930, and their three-dimensional dose cloud may be computed and analyzed by the Interplant® system. The number of seeds found may be different from the actual number of implanted seeds, so the activity of seeds may be adjusted so that the analysis shows the distribution of truly implanted dose. Finally, the remainder of the treatment plan is updated, in order to maintain to maintain optimal dose coverage of the prostate. For visual evaluation of the registration performed in step 1030, fiducial pattern 1310 and other reconstructed structures may be projected back to the coordinate frame of TRUS probe 930 and superimposed in the 3D view provided by the Interplant® system.

As well as being used for intra-operative seed matching and registration, process 1000 could be extended to post-operative care. In this approach, the last available implant plan could be projected onto post-operative images and the individual seeds would be matched. The software running on data system 955 may repeat imaging sessions regularly over an expanded period of time. As a result, it is possible to track the path of each individual seed, which could provide an insight to how the prostate changes shape, volume, and pose over time. Having collected data from a sufficiently large number of patients, the software may predict statistical motion of seeds with respect to the relevant anatomy. This may prove to be helpful in understanding the process of post-operative edema, a crucially important issue in prostate brachytherapy. The efficacy of projecting prior information to new X-ray images can be greatly facilitated by synchronizing the insertion sequence with the poses of C-arm fluoroscope 910, so that the newly inserted seeds are less likely obscure each other. This condition can be easily met if the implant is executed by rows of needles and images are acquired by C-arm fluoroscope 910 after every row.

Figure 18:
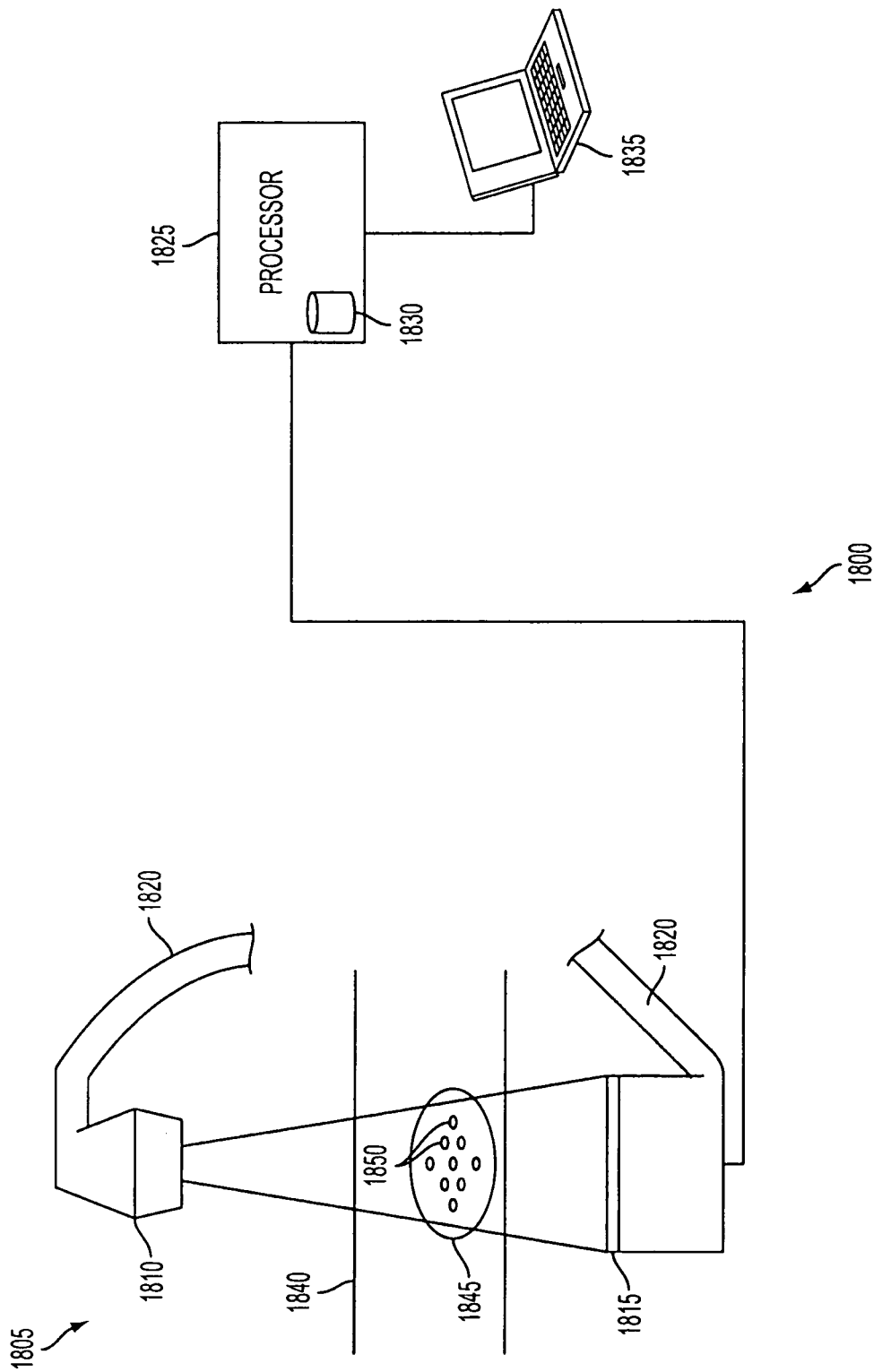
FIG. 18 illustrates an exemplary system for performing seed reconstruction according to the present invention.

FIG. 18 illustrates an exemplary system 1800 for registering objects, such as brachytherapy seeds, in a 3-D image space using images acquired at multiple poses of a single 2-D medical imaging system. System 1800 may provide for tracking of a C-arm fluoroscope (or some other imaging modality) and for reconstruction and registration of a plurality of objects, such as brachytherapy seeds, without the use of an external tracker. System 1800 includes a C-arm fluoroscope 1805 having a transmitter 1810 and a detector array 1815, which are mounted to a gimbal 1820. Detector array 1815 is connected to a processor 1825 that has a memory 1830 encoded with software (hereinafter "seed reconstruction software") that implements processes associated with the present invention. User interface 1835 is connected to processor 1825.

C-arm fluoroscope 1805 acquires images of an anatomical region of interest 1845 within a patient 1840. Implanted within anatomical region of interest 1845 is a plurality of seeds 1850. Using gimbal 1820, C-arm fluoroscope acquires multiple fluoroscopy images of anatomical region of interest 1845 at multiple orientations or poses.

Figure 19:
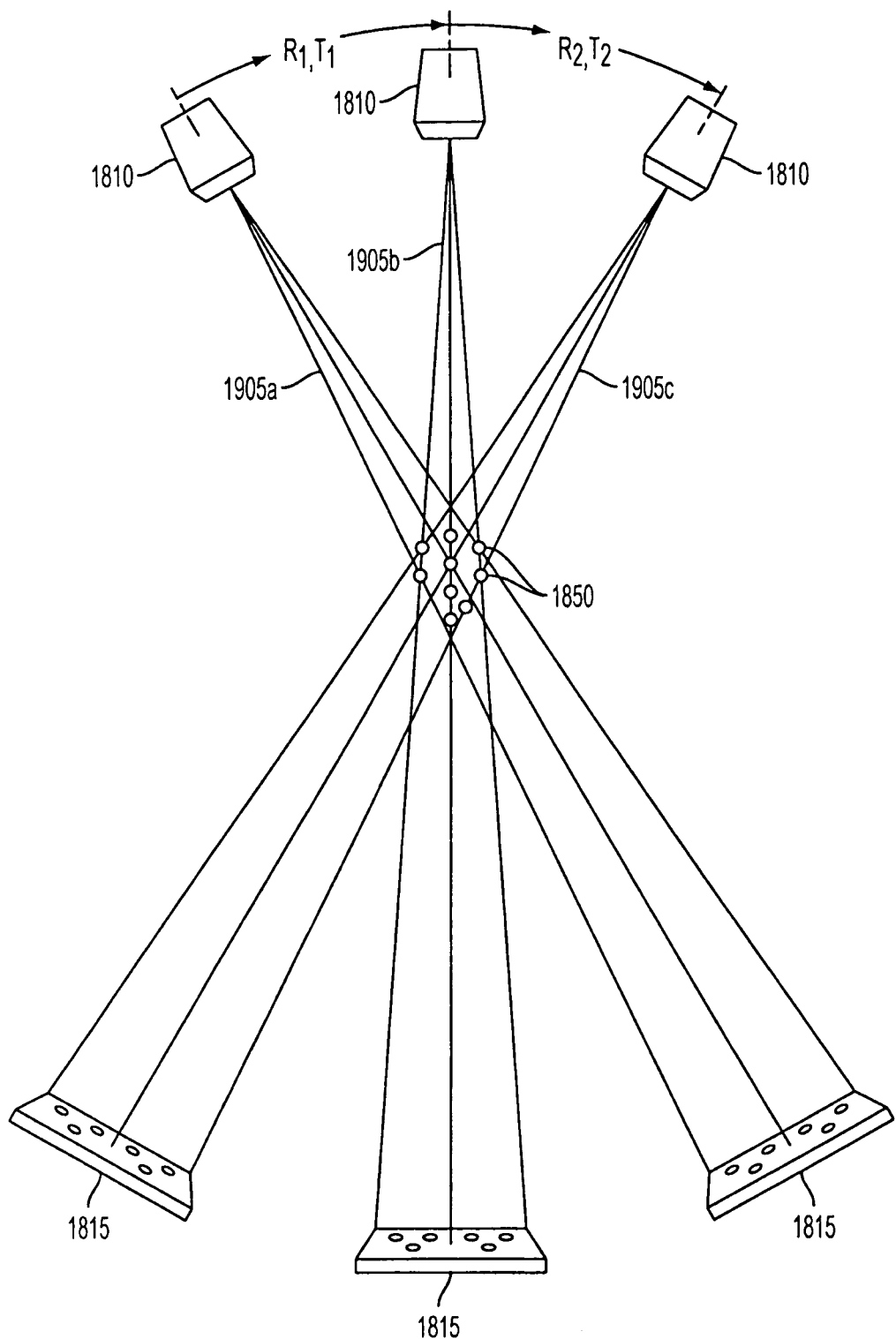
FIG. 19 illustrates three C-arm images of a plurality of seeds acquired at different poses.

FIG. 19 illustrates three exemplary images acquired of seeds 1850 acquired at a first pose 1905*a*, a second pose 1905*b*, and a third pose 1905*c*. Gimbal 1820 orients transmitter 1810 and detector array 1815 to provide an image of seeds 1850 at each pose 1905*a-c*. As illustrated in FIG. 19, pose 1905*b* differs from pose 1905*a* by a rotation $R_1$ and a translation $T_1$; and pose 1905*c* differs from pose 1905*b* by rotation $R_2$ and translation $T_2$.

Figure 20:
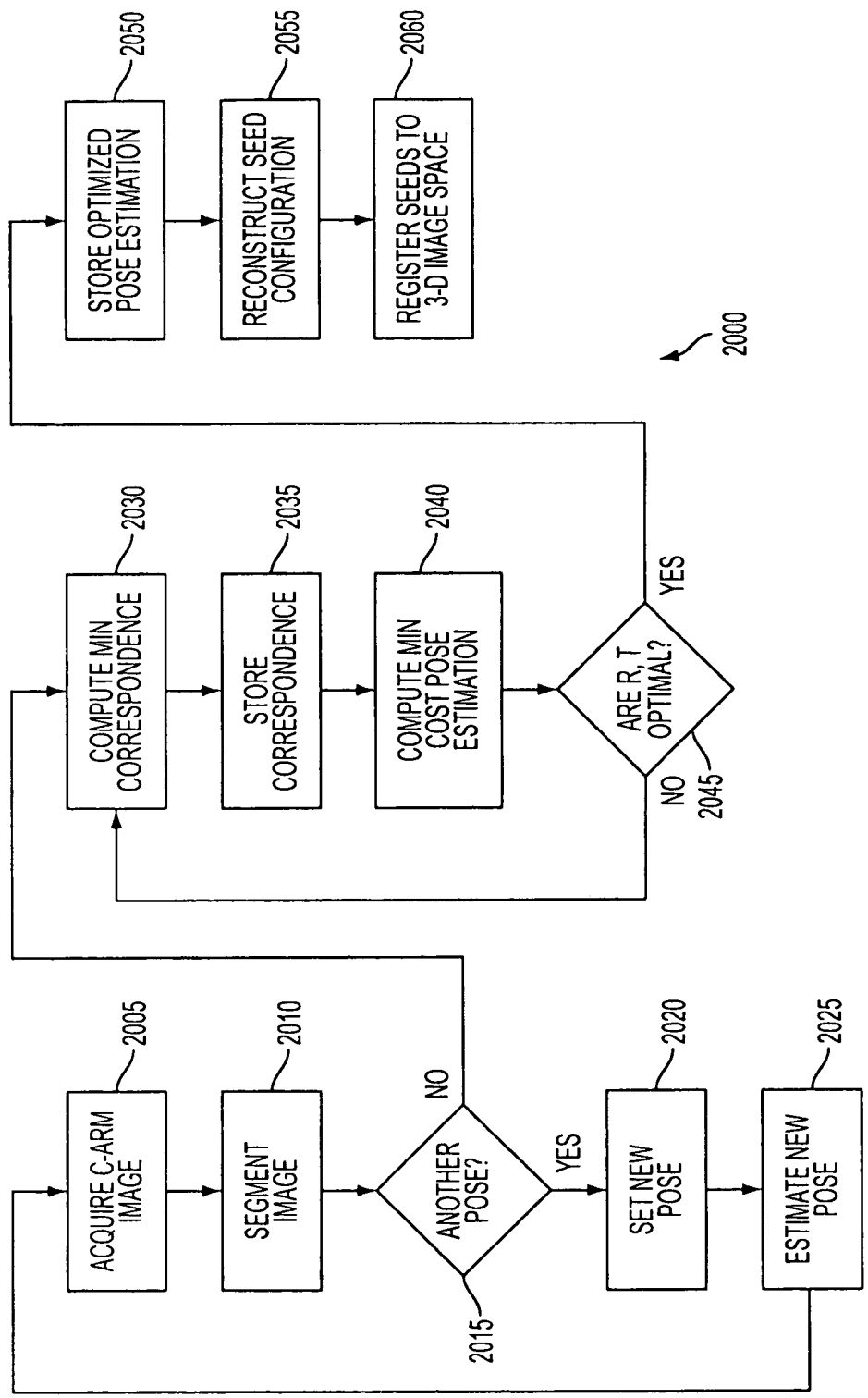
FIG. 20 illustrates an exemplary process for registering objects in a 3-D image space using images acquired at multiple poses with a single 2-D medical imaging system.

FIG. 20 is a diagram of an exemplary process 2000 for registering objects in a 3-D image space using images acquired at multiple poses of a single 2-D medical imaging system. Process 2000 may be performed all or in part by the seed reconstruction software running on processor 1825 in conjunction with user interaction via interface 1835. At the initiation of process 2000, C-arm fluoroscope ready to acquire images of anatomical region of interest 1845 (and seeds 1850) within the field of view of detector array 1815. Further, an initial pose estimation of C-arm fluoroscope 1805 may be provided and stored in memory 1830. The initial pose estimation may be an estimated rotation and translation from some default baseline orientation and position.

In step 2005, C-arm fluoroscope 1815 acquires an image of anatomical region of interest 1845 containing seeds 1850. In doing so, the user may input a command via user interface 1835. The seed reconstruction software receives the command and in turn issues the appropriate instructions to transmitter 1810 and detector array 1815 to acquire an image. The seed reconstruction software receives image data from detector array 1815 and stores the data values in memory 1830.

In step 2010, the seed reconstruction software segments the image acquired in step 2005. In doing so, the seed reconstruction software may implement any of a number of segmentation image processing algorithms that are capable of identifying the pixels that correspond to seeds 1850. The seed reconstruction software stores the segmented seed information in memory 1830.

In step 2015, the seed reconstruction software determines if another image at another C-arm image (at another pose) is to be acquired. For example, three C-arm images, each at a different pose 1905a-c may be acquired and used to reconstruct seeds 1850 and register them to a 3-D image space. More or fewer images may be acquired and used. Although more C-arm images, acquired at different poses, may increase the accuracy and precision of the reconstruction and registration of seeds 1850, this occurs at the expense of computation time. In general, three images at poses 1905a-c may strike a balance between accuracy/precision and computation time. Variations in the number of images and poses may vary, depending on the complexity and geometry of seeds 1850 and the computational power of processor 1825. One skilled in the art will readily appreciate that such variations to process 2000 are possible and within the scope of the invention.

If another image is to be acquired at another pose, process 2000 proceeds via the "yes" branch of step 2015 and proceeds to step 2020.

In step 2020, C-arm fluoroscope 1805 is positioned at a new pose. To do this, the seed reconstruction software may issue commands to an actuator (not shown) coupled to gimbal 1820 of C-arm fluoroscope 1805 to achieve a new pose. Alternatively, a user may command the actuator to a new pose via user interface 1835.

In step 2025, the new pose is estimated. If the seed reconstruction software issued the command to C-arm fluoroscope 1805 in step 2020, the new pose estimate may be the commanded pose. Similarly, if the user provided the command to C-arm fluoroscope 1805 via user interface 1835, then the user-provided command may be the new pose estimate. In either case, the seed reconstruction software may store the estimated pose, and the estimated transformation from the previous pose to the present pose. Referring to FIG. 19, the transformation from pose 1905a to pose 1905b, for example, may be represented as rotation $R_1$ and translation $T_1$. Rotation $R_1$ may be represented as rotation matrix or a quaternion. Translation $T_1$ may be represented as a vector. The pose estimation, which includes rotation $R_1$ and translation $T_1$, may be a rough estimate. Accordingly, C-arm fluoroscope 1805 does not require an external tracker.

Having established a new pose for C-arm fluoroscope 1805 in step 2020, and having stored pose estimates in step 2025, the seed reconstruction software may repeat steps 2005 and 2010. Accordingly, after multiple iterations of steps 2005-2025, multiple images are stored in memory 1830, each of which having a corresponding pose estimation.

Returning to step 2015, if no more images are to be acquired, process 2000 proceeds via the "no" branch of step 2015 and proceeds to step 2020.

In step 2030, the seed reconstruction software computes a minimum cost correspondence between the segmented seeds imaged in steps 2005 and segmented in step 2010. The seed reconstruction software may do so by finding the minimum of the following relation:

$$\underset{R,\,T,\,M,\,f}{\operatorname{argmin}} \sum_{i=1}^{N_1} \sum_{j=1}^{N_2} \sum_{k=1}^{N_3} C_{i,j,k} f_{i,j,k}$$

where $N_1$, $N_2$, $N_3$ respectively refer to the number of seeds segmented in the first, second, and third image; R is a combined rotation matrix, which includes rotations $R_1$ and $R_2$; T is a combined translation vector, which includes translations $T_1$ and $T_2$; $C_{i,j,k}$ is a cost factor of matching the ith seed segmented in the first image with the jth seed segmented in the second image with the kth seed segmented in the third image; and M is the projection model of C-arm fluoroscope 1805. The projection model M refers to the spatial calibration parameters of C-arm fluoroscope 1805. The projection model M is typically approximated as a five-parameter projection camera model, which may be assumed constant for purposes of the present invention.

The term $f_{i,j,k}$ is a binary variable that denotes a correspondence between the the ith seed segmented in the first image with the jth seed segmented in the second image with the kth seed segmented in the third image. In other words, f is a matrix that maps each seed segmented in one image with its counterpart in the other images.

In computing the minimum cost correspondence in step 2030, the seed reconstruction software iteratively selects a given correspondence $f_{i,j,k}$, and then computes its associated cost factor $C_{i,j,k}$. The associated cost factor $C_{i,j,k}$ is a function of the combined rotation matrix R and the combined translation vector T, both of which are derived from the rotations $R_1$ and $R_2$ and translations $T_1$ and $T_2$ estimated in step 2025.

The seed reconstruction software may compute the cost factor $C_{i,j,k}$ associated with a given correspondence $f_{i,j,k}$ by computing a projection error for the given correspondence. The seed reconstruction software may do this by generating a line from the segmented seed in each image to transmitter 1810 of C-arm fluoroscope according to projection model M. The seed reconstruction software then computes an intersection point in 3-D space at the intersection of these generated lines. Then, the seed reconstruction software projects this 3-D point onto detector array 1815 according to the pose estimations determined in step 2025. Then, for each projection, the seed reconstruction software computes the distance from the projected point in the corresponding image to the segmented seed in that image. In doing so, the seed reconstruction software computes three error distances, one for each pose and corresponding image, which it may average to compute cost factor $C_{i,j,k}$.

The seed reconstruction software may compute the cost factor $C_{i,j,k}$ for each segmented seed (the ith seed segmented in the first image with the jth seed segmented in the second image with the kth seed segmented in the third image) for all possible correspondences $f_{i,j,k}$. However, given all the possible combinations, this may be considered an "NP-Hard" combinatorial optimization problem. To improve computational efficiency, the seed reconstruction software may use a network flow-based combinatorial optimization solution, as discussed above.

Further to step 2030, the seed reconstruction software computes the summed cost factors $C_{i,j,k}$, resulting in a summed cost C for each correspondence $f_{i,j,k}$. The correspondence associated with the lowest summed cost C is the minimum cost correspondence.

In step 2035, having solved for the minimum cost correspondence $f_{i,j,k}$ in step 2030, the seed reconstruction software may store the minimum cost correspondence $f_{i,j,k}$ in memory 1830.

In step 2040, the seed reconstruction software computes a minimum cost pose estimation corresponding to the minimum cost correspondence $f_{i,j,k}$ computed in step 2035. In doing so, the seed reconstruction software may select a plurality of combined rotation matrices R and a plurality of combined translation vectors T, each of which have values that vary from those of the pose estimation generated in step 2025. The number of values, the range by which the values vary from the pose estimation generated in step 2025, and the spacing of the values, may be stored in memory 1830 as configuration parameters. These configuration parameters may be provided by the user via user interface 1835.

In step 2040, the seed reconstruction software computes a minimum cost pose estimation, by which it computes the combined rotation matrix R and combined translation vector T according to the relation described above with respect to step 2030

$$\underset{R,\,T,\,M,\,f}{\operatorname{argmin}} \sum_{i=1}^{N_1} \sum_{j=1}^{N_2} \sum_{k=1}^{N_3} C_{i,j,k} f_{i,j,k}.$$

In this step, correspondence $f_{i,j,k}$ is set to that computed in step 2030, and the combined rotation matrix R and combined translation vector T are varied. For each iteration of R and T, the seed reconstruction software may compute the associated cost factor $C_{i,j,k}$ of the ith seed segmented in the first image with the jth seed segmented in the second image with the kth seed segmented in the third image. The seed reconstruction software may do so by computing a projection error in the same or similar manner as described with regard to step 2030 above. For each iteration of R and T, the seed reconstruction software computes a summed cost factor C according to the relation above. The seed reconstruction software then selects the pose estimation associated with the lowest summed cost factor C. Step 2040 results in a minimum cost pose estimation, which is in the form of combined rotation matrix R and combined translation vector T, which in turn corresponds to a best estimation for rotations $R_1$ and $R_2$ and translations $T_1$, and $T_2$, associated with the correspondence $f_{i,j,k}$ computed in step 2030.

In step 2045, the seed reconstruction software determines if the pose estimation computed in step 2040 is optimal. In doing so, the seed reconstruction software compares the lowest summed cost C computed in step 2040 with an expected minimum cost. The expected minimum cost may be stored in memory 1830 as a configuration parameter. Alternatively, the seed reconstruction software may display the lowest summed cost C computed in step 2040 to the user via user interface 1835. In this case, the user may decide if the minimum cost pose estimation computed in step 2040 is optimal, or if the process should be repeated with a new correspondence $f_{i,j,k}$.

If it is determined that the pose estimation computed in step 2040 is not optimal, then process 2000 proceeds via the "no" branch of step 2045 to repeat steps 2030-2040. In the subsequent execution of step 2030, the seed reconstruction software computes a new minimum correspondence (step 2030) corresponding to the new pose estimation computed in step 2050. With this new minimum correspondence, the seed reconstruction software computes a new minimum cost pose estimation (step 2040). Accordingly, the loop of steps 2030-2045 may be iterated whereby each iteration may converge on an optimal solution for the correspondence and the pose estimation.

If it is determined that the pose estimation computed in step 2040 is optimal, then process 2000 proceeds via the "yes" branch of step 2045 to step 2050.

In step 2050, the seed reconstruction software stores the minimum cost pose estimation computed in step 2040 in memory 1830.

In step 2055, the seed reconstruction software reconstructs the plurality of seeds 1850 in a three-dimensional space using the first, second, and third segmented images, along with the minimum cost correspondence and minimum cost post estimation between the images. In doing so, the seed reconstruction software may assign x, y, and z coordinates to each of the segmented seeds 1850 in a coordinate space. The coordinate space may be referenced to the optical axis of C-arm fluoroscope 1805, although other coordinate references may be used.

In step 2060, the seed reconstruction software may register the reconstructed three-dimensional segmented seeds 1850 to a three-dimensional image space corresponding to an image acquired by a three-dimensional imaging modality, such as an ultrasound imager, and the like.

Variations to system 1800 and process 2000 are possible. For example, if the plurality of seeds 1850 are insufficient to enable process 2000 to yield a sufficiently precise minimum cost pose estimation, then additional objects may be introduced, such as a wire or metal beads, by attaching them to the skin of patient 1840, and within the field of view of detector array 1815 for each of poses 1905a-c. Further, if necessary, a fiducial device may be introduced having a feature, such as an ellipse of fiducial device 105 illustrated in FIG. 1.

Further, although the descriptions of system 1800 and process 2000 involve a C-arm fluoroscope, one skilled in the art will readily appreciate that the reference to a C-arm fluoroscope is exemplary, and that any two-dimensional medical imaging modality may be used provided that the imaging modality enables image acquisition of anatomical region of interest 1845 from multiple orientations or poses.

Additionally, although system 1800 and process 2000 involve imaging, segmenting, and reconstructing seeds 1850, such as brachytherapy seeds, one skilled in the art will readily recognize that other objects may be substituted for the seeds 1850 described herein. Other objects may include surgical tools, foreign objects, or any other plurality of objects within anatomical region of interest 1845 within patient 1840, wherein the objects are visible to C-arm fluoroscope 1805 (or other imaging modality, as stated above) with sufficient contrast to be segmented using known segmentation techniques.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:
1. A system for registering images from two medical imaging modalities comprising:
 a first imager having a first coordinate frame;
 a second imager having a second coordinate frame; and
 a data system, wherein the data system includes a non-transitory computer readable medium encoded with computer instructions for performing an image registration process including:
  acquiring a first image from the first imager;
  acquiring a second image from the second imager;
  determining a first coordinate transformation between the first coordinate frame and a fiducial coordinate frame corresponding to a fiducial; and
  registering the first image to the second coordinate frame,
  wherein the determining the first coordinate transformation includes:
    providing a current estimated coordinate transformation;
    generating a current estimated image corresponding to the current estimated coordinate transformation;
    determining an error function between the first image and the current estimated image;
    determining a multidimensional derivative corresponding to the current estimated coordinate transformation; and
    determining a new estimated coordinate transformation corresponding to the error function and the multidimensional derivative.

2. The system of claim 1, wherein the first imager is a C-arm fluoroscope.

3. The system of claim 1, wherein the second imager is an ultrasound system.

4. The system of claim 1, wherein the fiducial includes a Tantalum wire.

5. The system of claim 1, wherein the image registration process further includes: acquiring a third image from the first imager;
  determining a second coordinate transformation between the first coordinate frame and the fiducial coordinate frame; and
  registering the third image to the second coordinate frame.

6. The system of claim 5, wherein the image registration process further includes:
  identifying an object in the first and third images; and
  locating the object in a three-dimensional space corresponding to the second coordinate frame.

7. The system of claim 6, wherein the image registration process further includes:
  displaying the object in the second image.

8. The system of claim 1, wherein the data system including the non-transitory computer readable medium encoded with computer instructions for performing the image registration process further includes:
  a fiducial having features visible to the first imager, the fiducial having the fiducial coordinate frame that has a known position and orientation relative to the second coordinate frame.

9. The system of claim 8, wherein the features include:
  a point;
  a line; and
  an ellipse.

10. The system of claim 9, wherein the features are arranged to provide a substantially distinct image corresponding to a viewing angle of the first imager.

11. A method for registering images from a first imaging modality to a second imaging modality, the method comprising:
  acquiring a first image from a first imager having a first coordinate frame;
  acquiring a second image from a second imager having a second coordinate frame;
  determining a first coordinate transformation between the first coordinate frame and a fiducial coordinate frame corresponding to a fiducial; and
  registering the first image to the second coordinate frame according to the first coordinate transformation;
  wherein the determining the first coordinate transformation includes:
    providing a current estimated coordinate transformation;
    generating a current estimated image corresponding to the current estimated coordinate transformation;
    determining an error function between the first image and the current estimated image;
    determining a multidimensional derivative corresponding to the current estimated coordinate transformation; and
    determining a new estimated coordinate transformation corresponding to the error function and the multidimensional derivative.

12. The method of claim 11, further comprising:
  moving the first imager;
  acquiring a third image from the first imager;
  determining a second coordinate transformation between the first coordinate frame and the fiducial coordinate frame; and
  registering the third image to the second coordinate frame according to the second coordinate transformation.

13. The method of claim 11, further comprising:
  identifying an object in the first and third images; and
  determining a location of the object in a three-dimensional space corresponding to the second coordinate frame.

14. The method of claim 13, wherein the identifying an object in the first and third images includes:
  generating a plurality of network flows corresponding to a plurality of objects in the first and third images;
  determining a cost corresponding to each network flow;
  selecting the network flow corresponding to the least cost; and
  selecting the object from the plurality of objects corresponding the selected network flow.

15. The method of claim 11, further comprising:
  comparing the error function with a pre-determined error threshold; and
  selecting a final estimated coordinate transformation based on the comparing.

* * * * *